United States Patent
Bordon-Pallier et al.

(10) Patent No.: US 7,476,670 B2
(45) Date of Patent: Jan. 13, 2009

(54) PURINE DERIVATIVES, METHOD FOR PREPARING, PHARMACEUTICAL COMPOSITIONS AND NOVEL USE

(75) Inventors: Florence Bordon-Pallier, Guyancourt (FR); Jean-Luc Haesslein, Jassans-Riottier (FR)

(73) Assignee: Aventis Pharma S.A., Antony (FR)

( * ) Notice: Subject to any disclaimer, the term of this patent is extended or adjusted under 35 U.S.C. 154(b) by 790 days.

(21) Appl. No.: 10/780,018

(22) Filed: Feb. 17, 2004

(65) Prior Publication Data

US 2007/0185140 A1 Aug. 9, 2007

Related U.S. Application Data

(60) Provisional application No. 60/468,726, filed on May 7, 2003.

(30) Foreign Application Priority Data

Feb. 18, 2003 (FR) .................. 03 01915

(51) Int. Cl.
C07D 473/34 (2006.01)
A61K 31/52 (2006.01)
A61P 35/00 (2006.01)
A61P 25/28 (2006.01)

(52) U.S. Cl. .............. 514/234.2; 514/263.2; 544/118; 544/276; 544/277

(58) Field of Classification Search .......... 514/234.2, 514/263.2; 544/118, 277, 276
See application file for complete search history.

(56) References Cited

U.S. PATENT DOCUMENTS

2003/0008841 A1* 1/2003 Devos et al. .............. 514/45
2007/0049591 A1* 3/2007 Pinkerton et al. ........ 514/234.5

FOREIGN PATENT DOCUMENTS

| WO | WO 92/12718 | 8/1992 |
|----|-------------|--------|
| WO | WO 00/44750 | 8/2000 |
| WO | WO02051843  | 7/2002 |

OTHER PUBLICATIONS

M'barek Haidoune et al., J. Het Chem vol. 31, pp. 1461-1464 (1994).*

* cited by examiner

*Primary Examiner*—Mark L Berch
(74) *Attorney, Agent, or Firm*—Kelly L. Bender

(57) ABSTRACT

The invention relates to novel products of formula (I):

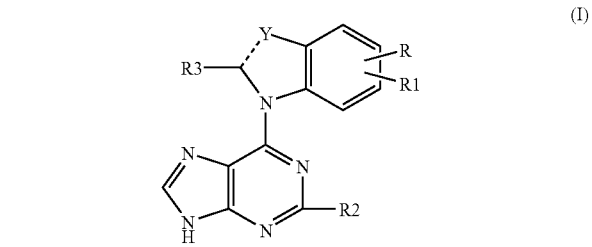

in which:

Y represents N, O, S, CHR3 or =CR3 the dashed line representing a single or double bond, R and R1 represent in particular H, Hal, OH, alkyl, alkoxy, cyano, $NO_2$, NR4R5, trifluoromethyl, trifluoromethoxy, aryl, heteroaryl, —S(O)n-NR4R5 with n representing 0 to 2, acyl, —NH—CO-alkyl or —NH—CO—NH-phenyl, R3 represents H, Hal, alkyl, cyano, $NO_2$, NR4R5, trifluoromethyl or aryl, R2 represents R4, OR4, SR4 or NR4R5, R4 represents H, alkyl, cycloalkyl or aryl, either R4 and R5 are chosen from the values for R4, or R4 and R5 form, with N, a heterocyclic radical which may contain N, O and S, all these radicals being optionally substituted, these products being in all the isomeric forms and the salts, as medicinal products.

11 Claims, No Drawings

PURINE DERIVATIVES, METHOD FOR PREPARING, PHARMACEUTICAL COMPOSITIONS AND NOVEL USE

The present invention relates to novel purine derivatives, to the method for preparing them, to the novel intermediates obtained, to their application as medicinal products, to the pharmaceutical compositions containing them and to the novel use of such purine derivatives.

A subject of the invention is thus novel purine derivatives.

The products of the present invention have protein kinase-inhibiting properties.

Among the kinases inhibited, mention may in particular be made of cyclin-dependent protein kinases called 'cdk', in particular CDK1 and CDK2, GSK, GSK3Beta, CIV1, SARC, SRC kinase ( )Abl kinase, CAM kinase II, casein kinase II, EGF-tyrosine kinase, IRK kinase, Map kinase (ERK 42), MEK1 kinase, PKA, Protein kinase p56lck, Zap70, AKT; FAK, JNK3, PLK1.

Protein kinases are a family of enzymes which catalyze the phosphorylation of hydroxyl groups of specific protein residues such as tyrosine, serine or threonine residues. Such phosphorylations can widely modify the function of the protein; thus, protein kinases play an important role in regulating a large variety of cell processes, including in particular metabolism, cell proliferation, cell differentiation, cell migration or cell survival. Among the various of cell functions in which the activity of a protein kinase is involved, some processes represent attractive targets for treating cancer-related diseases and also other diseases.

Thus, one of the objects of the present invention is to provide compositions which have anticancer activity by acting in particular with respect to kinases. Among the kinases for which a modulation of the activity is sought, mention may in particular be made of FAK (Focal Adhesion Kinase).

FAK is a cytoplasmic tyrosine kinase which plays an important role in transduction of the signal transmitted by integrins, a family of heterodimeric cell adhesion receptors. FAK and the integrins are colocalized in perimembrane structures called adhesion plaques. It has been shown, in many cell types, that the activation of FAK, and also its phosphorylation on tyrosine residues and in particular its autophosphorylation on tyrosine 397, are dependent on binding of the integrins to their extracellular ligands and are therefore induced during cell adhesion [Kornberg L, et al. J. Biol. Chem. 267(33): 23439-442. (1992)]. The autophosphorylation on tyrosine 397 of FAK represents a binding site for another tyrosine kinase, Src, via its SH$_2$ domain [Schaller et al. Mol. Cell. Biol. 14: 1680-1688. 1994; Xing et al. Mol. Cell. Biol. 5: 413-421. 1994]. Src can then phosphorylate FAK on tyrosine 925, thus recruiting the adapter protein Grb2 and inducing, in some cells, activation of the ras and MAP Kinase pathway involved in the control of cell proliferation [Schlaepfer et al. Nature; 372:786-791. 1994; Schlaepfer et al. Prog. Biophy. Mol. Biol. 71:435-478. 1999; Schlaepfer and Hunter, J. Biol. Chem. 272:13189-13195. 1997]. The activation of FAK can also induce the jun NH$_2$-terminal kinase (JNK) signaling pathway and result in progression of the cells toward the G1 phase of the cell cycle [Oktay et al., J. Cell. Biol. 145: 1461-1469. 1999]. Phosphatidylinositol-3-OH kinase (PI3-kinase) also binds to FAK on tyrosine 397 and this interaction might be necessary for the activation of PI3-kinase [Chen and Guan, Proc. Nat. Acad. Sci. USA. 91: 10148-10152. 1994/Ling et al. J. Cell. Biochem. 73: 533-544. 1999]. The FAK/Src complex phosphorylates various substrates such as paxillin and p130CAS in fibroblasts [Vuori et al. Mol. Cell. Biol. 16: 2606-2613. 1996].

The results of many studies support the hypothesis that FAK inhibitors might be useful in the treatment of cancer. Studies have suggested that FAK might play an important role in cell proliferation and/or survival in vitro. For example, in CHO cells, some authors have demonstrated that overexpression of p125FAK leads to an acceleration in G1 to S transition, suggesting that p125FAK promotes cell proliferation [Zhao J.-H et al. J. Cell Biol. 143:1997-2008. 1998]. Other authors have shown that tumor cells treated with FAK anti-sense oligonucleotides lose their adhesion and enter into apoptosis (Xu et al, Cell Growth Differ. 4:413-418. 1996). It has also been demonstrated that FAK promotes cell migration in vitro. Thus, fibroblasts deficient for FAK expression (mice which are knockout for FAK) exhibit a rounded morphology and deficiencies in cell migration in response to chemotactic signals, and these deficiencies are suppressed by re-expression of FAK [D J. Sieg et al., J. Cell Science. 112: 2677-91, 1999]. Overexpression of the C-terminal domain of FAK (FRNK) blocks the elongation of adherent cells and reduces cell migration in vitro [Richardson A. and Parsons J. T. Nature. 380: 538-540, 1996]. Overexpression of FAK in CHO or COS cells or in human astrocytoma cells promotes cell migration. The involvment of FAK in promoting cell proliferation and migration in many cell types in vitro suggests a potential role for FAK in neoplastic processes. A recent study has effectively demonstrated an increase in tumor cell proliferation in vivo after induction of FAK expression in human astrocytoma cells [Cary L. A. et al. J. Cell Sci. 109: 1787-94, 1996; Wang D et al. J. Cell Sci. 113: 4221-4230, 2000]. In addition, immunohistochemical studies of human biopsies have demonstrated that FAK is overexpressed in prostate, breast, thyroid, colon, melanoma, brain and lung cancers, the level of expression of FAK being directly correlated with the tumors exhibiting the most aggressive phenotype [Weiner T M, et al. Lancet 342(8878): 1024-1025. 1993; Owens et al. Cancer Research 55: 2752-2755, 1995; Maung K. et al. Oncogene 18: 6824-6828, 1999; Wang D et al. J. Cell Sci. 113: 4221-4230, 2000].

Studying the molecular mechanisms which control the cell cycle has made it possible to demonstrate the role of the cdks thus defined: these Cdks are essential regulators of the cycle of cell division; cdks are proteins consisting of at least two subunits, a catalytic subunit (of which cdc2 is the prototype) and a regulatory subunit (cyclin). A certain number of cdks are thus known. Cdks therefore form protein complexes, each one of which is involved in a phase of the cell cycle.

Many documents in the literature describe the existence and the role of cdks and, by way of example, mention may in particular be made of document WO 97/20842.

Several kinase inhibitors have been described, such as butyrolactone, flavopiridol and 2(2-hydroxyethylamino)-6-benzylamino-9-methylpurine (called olomoucine).

Such Cdk-activating protein kinases are in particular those of pathogenic fungi which cause infectious diseases in a human organism.

In the context of the present invention, as pathogenic fungi, mention may be made of *Candida albicans*, but, for example, and equally: *Candida stellatoidea, Candida tropicalis, Candida parapsilosis, Candida krusei, Candida pseudotropicalis, Candida quillermondii, Candida glabrata, Candida lusianiae* or *Candida rugosa* or else mycetes of the *Saccharomyces cerevisiae* type, or of the *Aspergillus* or *Cryptococcus* type, and in particular, for example, *Aspergillus fumigatus, Coccidioides immitis, Cryptococcus neoformans, Histoplasma capsulatum, Blastomyces dermatitidis, Paracoccidioides brasiliens* and *Sporothrix schenckii* or else mycetes of the phycomycetes or eumycetes classes, in particular the subclasses of basidiomycetes, ascomycetes, mehiasco-mycetales (yeast) and plectascales, gymnascales (fungi of the skin and of the hair), or of the hyphomycetes class, in particular the subclasses conidiosporales and thallosporales, among which the following species: *mucor, rhizopus, coccidioides, paracoccidioides (blastomyces, brasiliensis), endomyces (blastomyces), aspergillus, menicilium (scopulariopsis), trichophyton, epidermophton, microsporon, piedraia, hormodendron, phialophora, sporotrichon, cryptococcus, candida, geotrichum, trichosporon* or else *toropsulosis, pityriasis Versicolor* or *Erythrasma*.

Among such pathogenic fungi, mention may be made most particularly of *Candida albicans*.

It may be noted that the first Cdk-activating kinases of fungi were identified in *Saccharomyces cerevisiae* and *Schizosaccharomyces pombe*. The activation of Cdks requires both the binding of a cycline molecule and the phosphorylation of the Cdk on a conserved threonine residue, located in a region referred to as 'T loop'. It has been shown that this phosphorylation is carried out by a kinase referred to as 'Cdk-activating kinase' or 'CAK'. By way of additional information regarding these 'CAKs', mention may be made of the contents of the documents referenced as follows:

'Solomon, Trends Biochem. Sci. 19, 496-500 (1994)
'Buck et al, EMBO J., 14(24), 6173-83 (1995)
'Damagnez et al, EMBO J., 14(24), 6164-72 (1995)

In the yeast *Saccharomyces cerevisiae*, a kinase responsible for CAK activity has been identified, and named CIV1.

By way of additional information regarding these 'CIV1's, mention may be made of the contents of the documents referenced as follows:

Thuret et al, Cell, 86(4), (1996)
Kaldis et al, Cell, 86(4), 553-564 (1996),
Espinosa et al, Science, 273(5282), 1714-1717 (1996)

Such a CAK activity as defined above, essential for cell survival and division, has been found and identified in pathogenic fungi such as in particular *Candida albicans*: the sequence of the gene encoding this CIV1 protein in *Candida albicans*, called CaCIV1, and the CaCIV1 protein, have been identified. Such a sequence and its protein are clearly defined in French patent application No. 9710287.

Such protein kinase inhibitors can in particular have antiproliferative properties.

Products of formula (I) as defined below which have fungal CIV1 protein kinase-inhibiting properties have now been found, these protein kinases being Cdk-activating, and this is in particular the subject of the present invention.

Thus, the present invention relates to products of formula (I) as defined below which can in particular have inhibitory properties for such a CIV1 protein which can be found in various fungi as defined above.

The present invention thus in particular relates to products of formula (I) as defined below which may have more particularly inhibitory properties for the CaCIV1 protein kinase of *Candida albicans* as defined above and described in French patent application No. 9710287.

Such inhibitors of a CIV1 protein essential for cell survival in yeasts can be used as antifungal agents, either as medicinal products or on an industrial scale.

Their inhibitory properties thus make it possible to use products of the present invention as fungicides for treating diseases caused by such pathogenic fungi.

The spectrum of known fungal infections extends from fungal attack of the skin or the nails to more serious mycotic infections of internal organs. Such infections and the diseases which result therefrom are identified as mycoses. Antimycotic substances with fungistatic or fungicidal effects are used to treat these mycoses.

The present invention also relates to the method for preparing such inhibitors, their use as an antifungal agent and the pharmaceutical compositions containing such inhibitors.

A subject of the present invention is thus the products of formula (I):

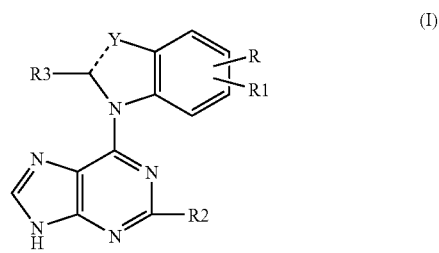

in which:

Y represents N, O, S, CHR3 or =CR3 the dashed line on the ring indicating that the corresponding bond is single or double, R and R1, which may be identical or different, represent hydrogen, halogen, hydroxyl, alkyl, alkoxy, cyano, $NO_2$, NR4R5, trifluoromethyl, trifluoromethoxy, aryl, heteroaryl, —S(O)n-NR4R5, acyl, —NH—CO-alkyl or —NH—CO—NH-phenyl in which the alkyl and phenyl radicals are optionally substituted with one or more radicals chosen from thienyl and phenyl, itself optionally substituted, these phenyl radicals themselves being optionally substituted with one or more radicals chosen from halogen atoms and the radicals —NH2, —NHAlk and —N(Alk)2, n represents an integer of 0 to 2, R3 represents hydrogen, halogen, alkyl, cyano, $NO_2$, NR4R5, trifluoromethyl, aryl, R2 represents a radical R4, OR4, SR4 or NR4R5 in which R4 represents a hydrogen atom or an alkyl, cycloalkyl or aryl radical, NR4R5 being such that either R4 and R5, which may be identical or different, are chosen from the values for R4 or R4 and R5 form, together with the nitrogen atom to which they are attached, a cyclic radical containing 4 to 6 ring members containing one or more hetero atoms, which may be identical or different, chosen from N, O and S, all the alkyl, alkoxy, cycloalkyl, aryl and heterocyclic radicals defined above being optionally substituted with one or more radicals chosen from halogen atoms, hydroxyl, cyano, trifluoromethyl, trifluoromethoxy, alkoxy, aryl and heterocyclic radicals, radicals with an acid or acid isostere function and the radicals —NHR4, —NalkR4, —COR4, —COOR4, CONalkR4 and —CONHR4 in which R4 has the meaning given above and alk represents an alkyl radical, all the aryl and heterocyclic radicals defined above also being optionally substituted with one or more alkyl, hydroxyalkyl and phenylalkyl radicals, all the aryl radicals defined above also being optionally substituted with a dioxol radical, all the alkyl and alkoxy radicals defined above being linear or branched and containing at most 6 carbon atoms, all the cycloalkyl radicals defined above containing at most 6 carbon atoms, said products of formula (I) being in all the possible racemic, enantiomeric and diastereoisomeric isomer forms, and also the pharmaceutically acceptable addition salts with inorganic and organic acids or with inorganic and organic bases of said products of formula (I).

A subject of the present invention is thus the products of formula (I) as defined above, in which Y represents N, O, S, CHR3 or =CR3
the dashed line on the ring indicating that the corresponding bond is single or double, R and R1, which may be identical or different, represent hydrogen, halogen, hydroxyl, alkyl, alkoxy, cyano, $NO_2$, NR4R5, trifluoromethyl, trifluoromethoxy, aryl, heteroaryl, —S(O)n-NR4R5, n represents an integer of 0 to 2, R3 represents hydrogen, halogen, alkyl, cyano, $NO_2$, NR4R5, trifluoromethyl, aryl, R2 represents a radical R4, OR4, SR4 or NR4R5 in which R4 represents a hydrogen atom or an alkyl, cycloalkyl or aryl radical, NR4R5 being such that either R4 and R5, which may be identical or different, are chosen from the values for R4 or R4 and R5 form, together with the nitrogen atom to which they are attached, a cyclic radical containing 4 to 6 ring members containing one or more hetero atoms, which may be identical or different, chosen from N, O and S, all the alkyl, alkoxy, cycloalkyl, aryl and heterocyclic radicals defined above being optionally substituted with one or more radicals chosen from halogen atoms, hydroxyl, cyano, trifluoromethyl, trifluoromethoxy, alkoxy, aryl and heterocyclic radicals, radicals with an acid or acid isostere function and the radicals —NHR4, —NalkR4, —COR4, —COOR4, —CONalkR4 and —CONHR4 in which R4 has the meaning given above and alk represents an alkyl radical, all the aryl and heterocyclic radicals defined above also being optionally substituted with one or more alkyl, hydroxyalkyl and phenylalkyl radicals, all the aryl radicals defined above also being optionally substituted with a dioxol radical, all the alkyl and alkoxy radicals defined above being linear or branched and containing at most 6 carbon atoms, all the cycloalkyl radicals defined above containing at most 6 carbon atoms, said products of formula (I) being in all the possible racemic, enantiomeric and diastereoisomeric isomer forms, and also the pharmaceutically acceptable addition salts with inorganic and organic acids or with inorganic and organic bases of said products of formula (I).

In the products of formula (I) and in the following text:

the term 'linear or branched alkyl radical' denotes methyl, ethyl, propyl, isopropyl, butyl, isobutyl, sec-butyl, tert-butyl, pentyl, isopentyl, hexyl and isohexyl radicals and also heptyl, octyl, nonyl and decyl radicals and their linear or branched positional isomers, the term 'linear or branched alkoxy radical' denotes methoxy, ethoxy, propoxy, isopropoxy and linear, secondary or tertiary butoxy radicals and pentoxy or hexoxy radicals and their linear or branched positional isomers, the term 'acyl or r-CO— radical' denotes a linear or branched radical containing at most 12 carbon atoms, in which the radical r represents a hydrogen atom, or an alkyl, cycloalkyl, cycloalkenyl, cycloalkyl, hetero-cycloalkyl, aryl or heteroaryl radical, these radicals having the optionally substituted values indicated above or below: thus, the acyl radical represents in particular CO-alkyl, CO-aryl or CO-heteroaryl. Mention may, for example, be made of formyl, acetyl, propionyl, butyryl or benzoyl radicals, or else valeryl, hexanoyl, acryloyl, crotonoyl, carbamoyl, pyrrolidinylcarboxy or furylcarboxy radicals, the term 'halogen atom' preferably denotes a chlorine atom, but may also represent a fluorine, bromine or iodine atom, the term 'cycloalkyl radical' denotes cyclopropyl and cyclobutyl radicals and most particularly cyclopentyl and cyclohexyl radicals, the term 'aryl radical' denotes unsaturated radicals, monocyclic radicals or radicals consisting of condensed rings which are carbocyclic. As examples of such an aryl radical, mention may be made of phenyl or naphthyl radicals, the term 'heterocyclic radical' denotes a saturated or unsaturated radical consisting at most of 6 ring members such that one or more of the ring members represents an oxygen, sulfur or nitrogen atom: such a heterocyclic radical thus denotes a carbocyclic radical interrupted with one or more hetero atoms chosen from oxygen, nitrogen and sulfur atoms, it being understood that the heterocyclic radicals can contain one or more hetero atoms chosen from oxygen, nitrogen and sulfur atoms and that, when these heterocyclic radicals comprise more than one hetero atom, the hetero atoms of these heterocyclic radicals may be identical or different. Mention may in particular be made of the dioxolane, dioxane, dithiolane, thiooxolane, thiooxane or piperazinyl radical, the piperazinyl radical substituted with a linear or branched alkyl radical containing at most 4 carbon atoms, the thienyl radical such as 2-thienyl and 3-thienyl, the furyl radical such as 2-furyl, the pyridyl radical such as 2-pyridyl, 3-pyridyl or 4-pyridyl, and the pyrimidyl, pyrrolyl, thiazolyl, isothiazolyl, diazolyl, triazolyl, tetrazolyl, thiadiazolyl, thiatriazolyl, oxazolyl, oxadiazolyl, 3-isoxazolyl or 4-isoxazolyl radical; mention may also be made of condensed heterocyclic groups containing at least one hetero atom chosen from sulfur, nitrogen and oxygen, for example benzothienyl such as 3-benzothienyl, benzofuryl, benzopyrrolyl, benzimidazolyl, benzoxazolyl, thionaphthyl, indolyl or purinyl. Mention may most particularly be made of thienyl radicals such as 2-thienyl and 3-thienyl, furyl radicals such as 2-furyl, and tetrahydrofuryl, thienyl, tetrahydrothienyl, pyrrolyl, pyrrolinyl and pyrrolidinyl radicals, the term 'acid or acid isostere function' denotes a free, salified or esterified carboxyl radical, a free or salified tetrazolyl radical, or the radicals:

—SO3H, —PO(OH)2, NH—SO2-CF3, —NH—SO2-NH—V, NH—SO2-NH—CO—V, NH—CO—V, —NH—CO—NH—V, —NH—CO—NH—SO2-V, —SO2-NH—, —SO2-NH—CO—V, —SO2-NH—CO—NH—V, —CO—NH—V, —CO—NH—OH, —CO—NH—SO2-V in which V represents a linear or branched alkyl or alkenyl radical containing at most 6 carbon atoms or a phenyl radical, these alkyl, alkenyl and phenyl radicals represented by V optionally being substituted with the substituents indicated above for the alkyl and phenyl radicals of the products of formula (I).

The carboxyl radical(s) of the products of formula (I) may be salified or esterified with diverse groups known to those skilled in the art, among which mention may, for example, be made of:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris-(hydroxymethyl)aminomethane, ethanolamine, pyridine, picoline, dicyclohexylamine, morpholine, benzylamine, procaine, lysine, arginine, histidine or N-methyl-glucamine, among the esterification compounds, the alkyl radicals for forming alkoxycarbonyl groups such as, for example, methoxycarbonyl, ethoxycarbonyl, tertbutoxycarbonyl or benzyloxycarbonyl, these alkyl radicals possibly being substituted with radicals chosen, for example, from halogen atoms, and hydroxyl, alkoxy, acyl, acyloxy, alkylthio, amino or aryl radicals such as, for example, in chloromethyl, hydroxypropyl, methoxymethyl, propionyloxymethyl, methylthiomethyl, dimethylaminoethyl, benzyl or phenethyl groups.

The addition salts with inorganic or organic acids of the products of formula (I) may, for example, be the salts formed with hydrochloric, hydrobromic, hydriodic, nitric, sulfuric, phosphoric, propionic, acetic, trifluoroacetic, formic, benzoic, maleic, fumaric, succinic, tartaric, citric, oxalic, glyoxylic, aspartic or ascorbic acids, alkylmonosulfonic acids such as, for example, methanesulfonic acid, ethanesulfonic acid or propanesulfonic acid, alkyldisulfonic acids such as, for example, methanedisulfonic acid, alpha,beta-ethane-disulfonic acid, arylmonosulfonic acids such as benzenesulfonic acid, and aryldisulfonic acid.

It may be recalled that stereoisomerism can be defined, in its broad sense, as the isomerism of compounds having the same structural formulae, but the various groups of which are arranged differently in space, such as, in particular, in monosubstituted cyclohexanes, the substituent of which may be in the axial or equatorial position, and the various possible rotational conformations of ethane derivatives. However, another type of stereoisomerism exists, due to the different spatial arrangements of substituents attached either on double bonds or on rings, which is often referred to as geometrical isomerism or cis-trans isomerism. The term 'stereoisomers' is used in the present application in its broadest sense and therefore concerns all of the compounds indicated above.

A particular subject of the present invention is the products of formula (I) as defined above, corresponding to formula (Ia):

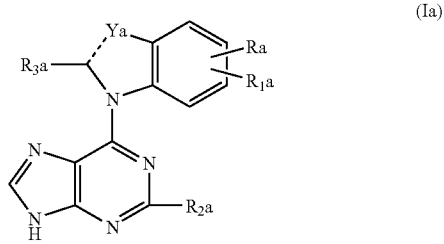

(Ia)

in which:

Ya represents N, O, S, CHR3a or =CR3a the dashed line on the ring indicating that the corresponding bond is single or double, Ra and R1a, which may be identical or different, represent hydrogen, halogen, hydroxyl, alkyl, alkoxy, cyano, NO$_2$, NR4aR5a, trifluoromethyl, trifluoromethoxy, phenyl, heteroaryl, —S(O)n-NR4aR5a, n represents an integer of 0 to 2, R3a represents hydrogen, halogen, alkyl, cyano, NO$_2$, amino, alkylamino, dialkylamino, trifluoromethyl and phenyl, R2a represents a radical R4a, OR4a, SR4a or NR4aR5a in which R4a represents a hydrogen atom or an alkyl, cycloalkyl or phenyl radical, NR4aR5a being such that either R4a and R5a, which may be identical or different, are chosen from the values for R4a, or R4a and R5a form, together with the nitrogen atom to which they are attached, an optionally substituted piperidyl, morpholinyl, pyrrolidinyl or piperazinyl radical, all the alkyl, alkoxy, cycloalkyl, phenyl, phenylalkyl and heterocyclic radicals defined above being optionally substituted with one or more radicals chosen from halogen atoms, hydroxyl, cyano, trifluoromethyl, trifluoromethoxy, alkoxy and phenyl radicals, a heterocyclic radical such as, for example, tetrahydropyranyl or piperidyl optionally substituted on N or C with a carboxyl radical which is free, salified or esterified with an alkyl radical, the radicals SO$_3$H, PO(OH)$_2$, NH—SO$_2$—CF$_3$, NH—SO$_2$—NH—V and NH—SO$_2$—NH—CO—V in which V represents a phenyl, alkyl or alkenyl radical, the alkenyl radicals being linear or branched containing at most 6 carbon atoms, and the radicals —NalkR4a, —NHR4a, —COR4a, —COOR4a, —CONalkR4a and —CONHR4a in which R4a has the meaning indicated above and alk represents an alkyl radical, all the phenyl and heterocyclic radicals defined above also being optionally substituted with one or more alkyl, hydroxyalkyl or phenylalkyl radicals, all the phenyl radicals defined above also being optionally substituted with a dioxol radical, all the alkyl and alkoxy radicals defined above being linear or branched and containing at most 6 carbon atoms, all the cycloalkyl radicals defined above containing 5 or 6 carbon atoms, said products of formula (Ia) being in all the possible racemic, enantiomeric and diastereoisomeric isomer forms, and also the pharmaceutically acceptable addition salts with inorganic and organic acids or with inorganic and organic bases of said products of formula (Ia).

It may be noted that, when R2a represents a radical NR4aR5a, R2a represents in particular the radical NH—Rya in which Rya represents the radical:

in which D1a and D2a, which may be identical or different, are either chosen from a hydrogen atom, a hydroxyl radical, linear or branched alkyl or alkoxy radicals containing at most 6 carbon atoms, and the radicals NHR5a, or together form the radical =O or =N—OR4a, R4a represents a hydrogen atom, or an alkyl, cycloalkyl or phenyl radical, R5a represents a hydrogen atom, an alkyl or cycloalkyl radical or the radical —COOtBu (Boc).

A more particular subject of the present invention is the products of formula (I) as defined above, corresponding to formula (Ib):

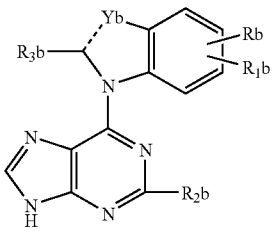

(Ib)

in which:

Yb represents N, CHR3b or =CR3b the dashed line on the ring indicating that the corresponding bond is single or double, Rb and R1b, which may be identical or different, represent hydrogen, halogen, hydroxyl, alkyl, alkoxy, cyano, NO$_2$, trifluoromethyl, trifluoromethoxy, phenyl, —S(O)n-NR4bR5b, n represents an integer of 0 to 2, R3b represents hydrogen, halogen, alkyl, cyano, NO$_2$, amino, alkylamino, dialkylamino, trifluoromethyl and phenyl, R2b represents a radical R4b or NR4bR5b in which R4b represents a hydrogen atom or an alkyl, cycloalkyl or phenyl radical, NR4bR5b being such that either R4b and R5b, which may be identical or different, are chosen from the values for R4b, or R4b and R5b form, together with the nitrogen atom to which they are attached, an optionally substituted piperidyl, morpholinyl or pyrrolidinyl radical, all the alkyl, alkoxy, cycloalkyl, phenyl and phenylalkyl radicals and heterocyclic radicals, such as piperidyl, morpholinyl and pyrrolidinyl, defined above being optionally substituted with one or two radicals chosen from halogen atoms, hydroxyl, cyano, trifluoromethyl, trifluoromethoxy, alkoxy and phenyl radicals, and tetrahydropyranyl and piperidyl radicals, themselves optionally substituted on N or C with a carboxyl radical which is free, salified or esterified with an alkyl radical, and the radicals —NalkR4a, —NHR4a and —COOR4a in which R4a has the meaning indicated above and alk represents an alkyl radical, all the phenyl and heterocyclic radicals defined above also being optionally substituted with one or more alkyl, hydroxyalkyl and phenylalkyl radicals, all the alkyl and alkoxy radicals defined above being linear or branched and containing at most 4 carbon atoms, all the cycloalkyl radicals defined above containing 5 or 6 carbon atoms, said products of formula (Ib) being in all the possible racemic, enantiomeric and diastereoisomeric isomer forms, and also the pharmaceutically acceptable addition salts with inorganic and organic acids or with inorganic and organic bases of said products of formula (Ib).

It may be noted that, when R2b represents a radical NR4bR5b, R2b represents in particular the radical NH—Ryb in which Ryb represents the radical:

in which D1b and D2b, which may be identical or different, are either chosen from a hydrogen atom, a hydroxyl radical, linear or branched alkyl and alkoxy radicals containing at most 4 carbon atoms, and the radicals NHR5b, or together form the radical =O or =N—OR4b, R4b represents a hydrogen atom, an alkyl radical containing at most 4 carbon atoms, phenyl, —CH$_2$-phenyl or a cycloalkyl radical containing at most 6 carbon atoms optionally substituted with the radical —NHR3b, R5b represents a hydrogen atom, an alkyl or cycloalkyl radical containing at most 6 carbon atoms, or the radial —COOtBu (Boc).

An even more particular subject of the present invention is the products of formula (I) as defined above, corresponding to formula (Ic):

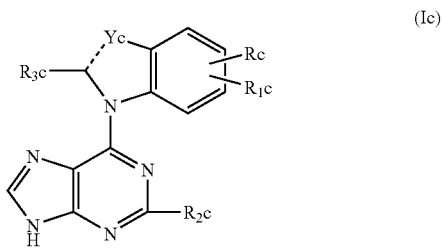

(Ic)

in which:

Yc represents N, CH$_2$ or CH=, the dashed line on the ring indicating that the corresponding bond is single or double, Rc and R1c, which may be identical or different, represent hydrogen, halogen, hydroxyl, alkyl, alkoxy, phenylalkoxy, phenylalkyl, cyano, NO$_2$, trifluoromethyl, trifluoromethoxy, phenyl, —S(O)n-NH2 optionally substituted on the nitrogen atom with one or two alkyl radicals and n represents an integer of 0 to 2, R3c represents hydrogen, halogen, alkyl, cyano, NO$_2$, trifluoromethyl and phenyl, R2c represents a radical NR4cR5c in which either R4c and R5c, which may be identical or different, are such that R4c represents a hydrogen atom or an alkyl, cycloalkyl, phenyl or phenylalkyl radical, the alkyl, cycloalkyl, phenyl and phenylalkyl radicals being optionally substituted with one or more radicals chosen from hydroxyl, amino or carboxyl which is free, salified or esterified with an alkyl radical, tetrahydropyrannyl radical or piperidyl radical, optionally substituted on N or C with a carboxyl radical which is free, salified or esterified with an alkyl radical, and R5c represents a hydrogen atom or an alkyl radical, or R4c and R5c form, together with the nitrogen atom to which they are attached, a piperidyl, morpholinyl or pyrrolidinyl radical, these radicals being optionally substituted with an alkyl, hydroxyalkyl, amino, monoalkylamino or dialkylamino radical, all the alkyl and alkoxy radicals defined above being linear or branched containing at most 4 carbon atoms, said products of formula (Ic) being in all the possible racemic, enantiomeric and diastereoisomeric isomer forms, and also the pharmaceutically acceptable addition salts with inorganic and organic acids or with inorganic and organic bases of said products of formula (Ic).

It may be noted that, when Ryc represents the radical:

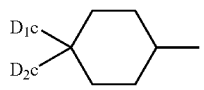

in which D1c and D2c, which may be identical or different, are either chosen from a hydrogen atom, a hydroxyl radical, linear or branched alkyl and alkoxy radicals containing at most 4 carbon atoms, and the radicals —NH$_2$, —NH—COOtBu or —NHalkyl in which the linear or branched alkyl radical contains at most 4 carbon atoms, or together form the radical =O or =N—Oalkyl, in which the linear or branched alkyl radical contains at most 4 carbon atoms.

Ryd represents in particular the radical:

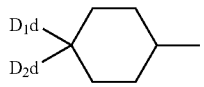

in which D1d and D2d, which may be identical or different, are chosen from a hydrogen atom, a hydroxyl radical, linear or branched alkyl and alkoxy radicals containing at most 4 carbon atoms, and the radicals —NH2, —NH—COOtBu or —NHalkyl in which the linear or branched alkyl radical contains at most 4 carbon atoms, or together form the radical =O or =N—Oalkyl, in which the linear or branched alkyl radical contains at most 4 carbon atoms.

Rye represents in particular the radical:

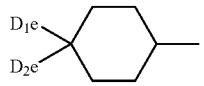

in which one of D1e and D2e represents a hydrogen atom and the other the radical —NH$_2$ optionally substituted with a radical —COOtBu or -alkyl in which the linear or branched alkyl radical contains at most 4 carbon atoms.

A most particular subject of the present invention is the products of formula (I) as defined above, corresponding to formula (Id):

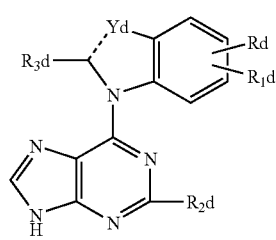

(Id)

in which:
Yd represents N, CH$_2$ or CH=,
the dashed line on the ring indicating that the corresponding bond is single or double, p0 Rd and R1d, which may be identical or different, represent hydrogen, halogen, alkyl, alkoxy, phenylalkoxy, NO$_2$, dialkylaminosulfonyl, —NH2, trifluoromethyl, —CO—CH3, —NH—CO-alkyl or —NH—CO—NH-phenyl in which the alkyl radical is optionally substituted with a thienyl or phenyl radical and the phenyl radical is optionally substituted with one or more radicals chosen from halogen atoms and the radicals —NH$_2$, —NHAlk and —N(Alk)2, R3d represents hydrogen or alkyl, R2d represents a radical NR4dR5d in which either R4d and R5d, which may be identical or different, are such that R4d represents a hydrogen atom, a linear or branched alkyl radical containing 1 to 4 carbon atoms and optionally substituted with one or two hydroxyl(s), a cycloalkyl radical optionally substituted with an amino or hydroxyl radical or a phenyl or phenylalkyl (1 to 4 C) radical with phenyl optionally substituted with a carboxyl radical which is free, salified or esterified with an alkyl radical, a tetrahydropyranalkyl radical (ex 28) or a piperidylalkyl radical (ex 31, 36) optionally substituted on N or C with a carboxyl radical, and R5d represents a hydrogen atom or an alkyl radical, or R4d and R5d form, together with the nitrogen atom to which they are attached, a piperidyl radical optionally substituted with an amino radical, a morpholinyl radical or a pyrrolidinyl radical (ex 34) optionally substituted with a hydroxyalkyl radical, all the alkyl and alkoxy radicals defined above being linear or branched containing at most 4 carbon atoms, said products of formula (Id) being in all the possible racemic, enantiomeric and diastereoisomeric isomer forms, and also the pharmaceutically acceptable addition salts with inorganic and organic acids or with inorganic and organic bases of said products of formula (Id).

A subject of the present invention is thus most particularly the products of formula (I) as defined above, corresponding to formula (Id) in which:

Yd represents N, CH$_2$ or CH=, the dashed line on the ring. indicating that the corresponding bond is single or double, Rd and R1d, which may be identical or different, represent hydrogen, halogen, alkyl, alkoxy, phenylalkoxy, NO$_2$, dialkylaminosulfonyl, R3d represents hydrogen or alkyl, R2d represents a radical NR4dR5d in which either R4d and R5d, which may be identical or different, are such that R4d represents a hydrogen atom, a linear or branched alkyl radical containing 1 to 4 carbon atoms and optionally substituted with one or two hydroxyl(s), a cycloalkyl radical optionally substituted with an amino or hydroxyl radical or a phenyl or phenylalkyl (1 to 4 C) radical with phenyl optionally substituted with a carboxyl radical which is free, salified or esterified with an alkyl radical, a tetrahydropyranalkyl radical or a piperidylalkyl radical optionally substituted on N or C with a carboxyl radical, and R5d represents a hydrogen atom or an alkyl radical, or R4d and R5d form, together with the nitrogen atom to which they are attached, a piperidyl radical optionally substituted with an amino radical, a morpholinyl radical or a pyrrolidinyl radical optionally substituted with a hydroxyalkyl radical, all the alkyl and alkoxy radicals defined above being linear or branched containing at most 4 carbon atoms, said products of formula (Id) being in all the possible racemic, enantiomeric and diastereoisomeric isomer forms, and also the pharmaceutically acceptable addition salts with inorganic and organic acids or with inorganic and organic bases of said products of formula (Id).

A most particular object of the present invention is the products of formula (I) as defined above, having the following names:

- trans-N-[6-(5,6-dichloro-2,3-dihydro-1H-indol-1-yl)-9H-purin-2-yl]-1,4-cyclohexanediamine dihydrochloride
- trans-N-[6-(1H-benzimidazol-1-yl)-9H-purin-2-yl]-1,4-cyclohexanediamine dihydrochloride
- trans-N-[6-(5,6-dimethyl-1H-benzimidazol-1-yl)-9H-purin-2-yl]-1,4-cyclohexanediamine
- trans-N-[6-(5,6-dichloro-1H-benzimidazol-1-yl)-9H-purin-2-yl]-1,4-cyclohexanediamine hydrochloride
- trans-N-[6-(5-methoxy-1H-benzimidazol-1-yl)-9H-purin-2-yl]-1,4-cyclohexanediamine dihydrochloride
- trans-N-[6-(1H-indol-1-yl)-9H-purin-2-yl]-1,4-cyclohexanediamine dihydrochloride
- trans-N-[6-[6-(phenylmethoxy)-1H-benzimidazol-1-yl]-9H-purin-2-yl]-1,4-cyclohexanediamine
- trans-N-[6-[5-(phenylmethoxy)-1H-benzimidazol-1-yl]-9H-purin-2-yl]-1,4-cyclohexanediamine
- trans-4-[[6-(1H-benzimidazol-1-yl)-9H-purin-2-yl]-amino] cyclohexanol
- trans-N-[6-(2,3-dihydro-5-nitro-1H-indol-1-yl)-9H-purin-2-yl]-1,4-cyclohexanediamine dihydrochloride
- trans-N-[6-(2,3-dihydro-6-(trifluoromethyl)-1H-indol-1-yl)-9H-purin-2-yl]-1,4-cyclohexanediamine (ex 40)
- trans-N-[1-[2-[(4-aminocyclohexyl)amino]-9H-purin-6-yl]-2,3-dihydro-1H-indol-5-yl]-2-thiopheneacetamide (ex 41)
- trans-N-[6-(6-nitro-2,3-dihydro-1H-indol-1-yl)-9H-purin-2-yl]-1,4-cyclohexanediamine (ex 44)

A subject of the present invention is also a method for preparing the products of formula (I) as defined above, wherein the compound of formula (II):

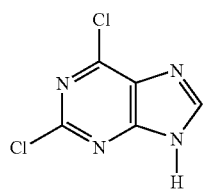
(II)

is subjected to the action of a compound of formula (III):

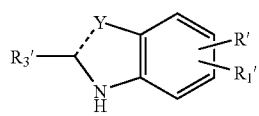
(III)

in which R', R1' and R3' have the meanings indicated respectively in claim 1 for R, R1 and R3, in which the optional reactive functions are optionally protected with protective groups, and Y has the meaning indicated in claim 1, so as to obtain a product of formula (IV):

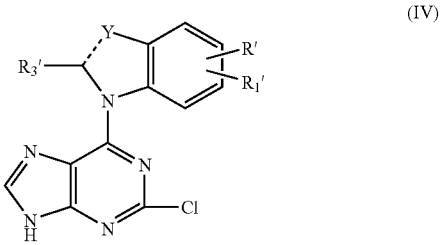
(IV)

in which R', R1', R3' and Y have the meanings indicated above, which product of formula (IV) is subjected to a reaction with a compound of formula (V):

R2'-H  (V)

in which R2' has the meaning indicated in claim 1 for R2 in which the optional reactive functions are optionally protected with protective groups, so as to obtain a product of formula (I'):

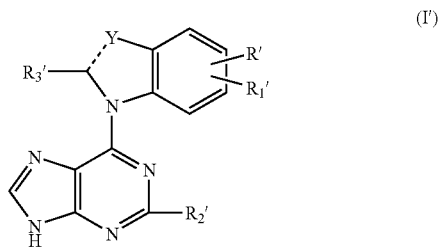
(I')

in which R', R1', R2', R3' and Y' have the meanings indicated above, the products of formula (I') having the meaning indicated in claim 1 for the products of formula (I) in which the optional reactive functions are optionally protected with protective groups, which products of formula (I') can be products of formula (I) and which, so as to obtain other product(s) of formula (I), can be subjected, if desired and if necessary, to one or more of the following conversion reactions, in any order:

a) a reaction of esterification of an acid function,
b) a reaction of saponification of an ester function to an acid function,
c) a reaction of oxidation of an alkylthio group to a corresponding sulfoxide or sulfone,
d) a reaction of conversion of a ketone function to an oxime function,
e) a reaction of reduction of the free or esterified carboxyl function to an alcohol function,
f) a reaction of conversion of an alkoxy function to a hydroxyl function, or else of a hydroxyl function to an alkoxy function,
g) a reaction of oxidation of an alkyl function to an aldehyde, acid or ketone function,
h) a reaction of conversion of a nitrile radical to a tetrazolyl,
i) a reaction of removal of protective groups which the protected reactive functions may carry, j) a reaction of salification with an inorganic or organic acid or with a base so as to obtain the corresponding salt, k) a reaction to resolve the racemic forms into resolved products, said products of formula (I) thus obtained being in all the possible racemic, enantiomeric and diastereoisomeric isomer forms.

The products of formula (I') having the meaning indicated above for the products of formula (I) in which the optional reactive functions are optionally protected with protective groups, which products of formula (I') can be products of formula (I) and which, so as to obtain other product(s) of formula (I), can be subjected, if desired and if necessary, to one or more of the following conversion reactions, in any order:

a) a reaction of esterification of an acid function, b) a reaction of saponification of an ester function to an acid function, c) a reaction of oxidation of an alkylthio group to a corresponding sulfoxide or sulfone, d) a reaction of conversion of a ketone function to an oxime function, e) a reaction of reduction of the free or esterified carboxyl function to an alcohol function, f) a reaction of conversion of an alkoxy function to a hydroxyl function, or else of a hydroxyl function to an alkoxy function, g) a reaction of oxidation of an alkyl function to an aldehyde, acid or ketone function, h) a reaction of conversion of a nitrile radical to a tetrazolyl, i) a reaction of removal of protective groups which the protected reactive functions may carry, j) a reaction of salification with an inorganic or organic acid or with a base so as to obtain the corresponding salt, k) a reaction to resolve the racemic forms into resolved products, said products of formula (I) thus obtained being in all the possible racemic, enantiomeric and diastereoisomeric isomer forms.

It may be noted that such reactions of conversion of the substituents to other substituents can also be carried out on the starting products and also on the intermediates as defined above, before continuing the synthesis according to the reactions indicated in the method described above.

Under preferential conditions for implementing the invention, the method described above can be carried out in the following way:

the product of formula (II) is therefore 2,6-dichloropurine, which is a commercially available product.

The product of formula (II) is subjected to the action of the product of formula (III) as defined above, in particular in an alcohol such as butanol, at a temperature of approximately 80° C. or at a temperature of approximately 75° C. for approximately 2 to 3 hours, or in DMF, so as to give a product of formula (IV) as defined above.

The product thus obtained, of formula (IV) as defined above, is subjected to the action of a compound of formula (V) under the conditions defined in the experimental section and in particular as indicated below.

The compound of formula (V) may in particular represent a compound of formula (XIV), (XV) or (XVI) as defined below:

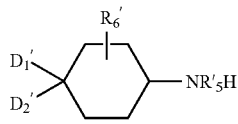

(XIV)

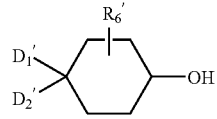

(XV)

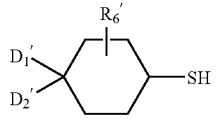

(XVI)

compounds of formula (XIV), (XV) or (XVI) in which $D_1'$, $D_2'$ and $R'_5$ have the meanings indicated in claim 1 respectively for D1, D2 and R5 in which the optional reactive functions are optionally protected with protective groups and R6' representing one or more substituents which the cycloalkyl radical may carry, in which the optional reactive functions are optionally protected with protective groups.

The product of formula (V), namely R2-H, may in particular represent the product (XIV):

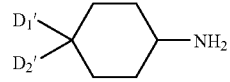

(XIV)

in which D1' and D2' have the meanings indicated above respectively for D1 and D2 in which the optional reactive functions are optionally protected with protective groups.

Thus, found among the products of formula (I') are in particular the products of formula (I"):

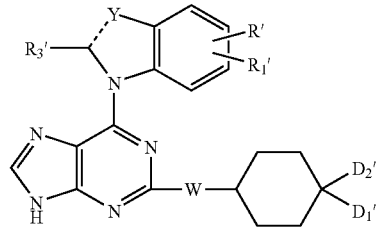

(I")

in which R', R1', R3', D1', D2' and Y' have the meanings indicated above, in which the optional reactive functions are optionally protected with protective groups, and W represents NH, S or O, which can be prepared in particular by reacting a product of formula (IV) as defined above with a product of formula (XIV), (XV) or (XVI) as defined above.

The reaction of the product of formula (IV) with a compound of formula (XIV), (XV) or (XVI) as defined above, so as to give a product of formula (I'), may in particular be carried out according to a condensation reaction which, where appropriate, may be carried out at a temperature of approximately 140° C. without solvent: such a condensation reaction may be followed by a reaction of salification in the presence of hydrochloric acid for example or else of tartaric acid, citric acid or methanesulfonic acid, in an alcohol such as, for example, ethanol or methanol, so as to give products of formula (I') as defined above.

The amine function of the compounds of formula (I') as defined above can be protected with a group such as Boc or CH$_2$-phenyl, and can then be freed under the usual conditions known to those skilled in the art.

The saponification reaction can be carried out according to the usual methods known to those skilled in the art, such as, for example, in a solvent such as methanol or ethanol, dioxane or dimethoxyethane, in the presence of sodium hydroxide or potassium hydroxide.

The reactions of reduction or oxidation of the product of formula (I') to a product of formula (I) can be carried out according to the usual methods known to those skilled in the art.

Depending on the values for Y', R', R1', R2', R3', D1', and D2', the products of formulae (I') may or may not constitute products of formula (I) and can give products of formula (I) or be converted into other products of formula (I) by being subjected to one or more of the reactions a) to k) indicated above.

Thus, the various reactive functions which some compounds of the reactions defined above may carry can, if necessary, be protected: these are, for example, free carboxyl, acyl or hydroxyl radicals or else amino and monoalkylamino radicals which can be protected with the appropriate protective groups.

The following nonexhaustive list of examples of protection of reactive functions may be mentioned:

the hydroxyl groups can be protected, for example, with alkyl radicals such as tert-butyl, trimethylsilyl, tert-butyldimethylsilyl, methoxymethyl, tetrahydropyranyl, benzyl or acetyl, the amino groups can be protected, for example, with acetyl, trityl, benzyl, tert-butoxycarbonyl, benzyloxycarbonyl or phthalimido radicals or other radicals known in peptide chemistry, the acyl groups, such as the formyl group, can be protected, for example, in the form of ketals or of thioketals which may be cyclic or noncyclic, such as dimethyl or diethyl ketal or ethylene dioxy ketal or diethyl thioketal or ethylene dithioketal, the acid functions of the products described above can, if desired, be amidated with a primary or secondary amine, for example in methylene chloride in the presence, for example, of 1-ethyl-3-(dimethylaminopropyl)carbodiimide hydrochloride at ambient temperature:

the acid functions can be protected, for example, in the form of esters formed with readily cleavable esters such as benzyl esters or tert-butyl esters or esters known in peptide chemistry.

The reactions to which the products of formula (I') as defined above can be subjected, if desired or if necessary, can be carried out, for example, as indicated below.

a) The products described above can, if desired, be the subject, on the optional carboxyl functions, of esterification reactions which can be carried out according to the usual methods known to those skilled in the art.

b) The optional conversions of ester functions to acid functions of the products described above can, if desired, be carried out under the usual conditions known to those skilled in the art, in particular by acid or alkaline hydrolysis, for example with sodium hydroxide or potassium hydroxide in an alcoholic medium, such as, for example, in methanol, or else with hydrochloric or sulfuric acid.

c) The optional alkylthio groups of the products described above can, if desired, be converted into the corresponding sulfoxide or sulfone functions under the usual conditions known to those skilled in the art, such as, for example, with peracids, such as, for example peracetic acid or meta-chloroperbenzoic acid, or else with oxone, sodium periodate in a solvent such as for example methylene chloride or dioxane, at ambient temperature.

The obtaining of the sulfoxide function can be promoted with an equimolar mixture of the product containing an alkylthio group and of the reagent such as in particular a peracid.

The obtaining of the sulfone function can be promoted with a mixture of the product containing an alkylthio group with an excess of the reagent such as in particular a peracid.

d) The reaction of conversion of a ketone function to an oxime function can be carried out under the usual conditions known to those skilled in the art, such as in particular action in the presence of an optionally O-substituted hydroxylamine in an alcohol such as, for example, ethanol, at ambient temperature or by heating.

e) The optional free or esterified carboxyl functions of the products described above can, if desired, be reduced to alcohol functions by the methods known to those skilled in the art: the optional esterified carboxyl functions can, if desired, be reduced to alcohol functions by the methods known to those skilled in the art and in particular with lithium aluminum hydride in a solvent such as, for example, tetrahydrofuran or else dioxane or ethyl ether.

The optional free carboxyl functions of the products described above can, if desired, be reduced to alcohol functions in particular with boron hydride derivatives.

f) The optional alkoxy functions, such as in particular methoxy functions, of the products described above can, if desired, be converted into hydroxyl functions under the usual conditions known to those skilled in the art, for example with boron tribromide in a solvent such as, for example, methylene chloride, with pyridine hydrobromide or hydrochloride, or else with hydrobromic or hydrochloric acid in water or trifluoroacetic acid at reflux.

g) The optional alcohol functions of the products described above can, if desired, be converted into aldehyde or acid functions by oxidation under the usual conditions known to those skilled in the art, such as, for example, by the action of manganese oxide so as to obtain aldehydes or of Jones reagent so as to obtain acids.

h) The optional nitrile functions of the products described above can, if desired, be converted into tetrazolyl under the usual conditions known to those skilled in the art, such as, for example, by cyclo-addition of a metal azide, such as, for example, sodium azide or an azide of trialkyltin, onto the nitrile function, as indicated in the method described in the article referenced as follows:

J. Organometallic Chemistry 33, 337 (1971) KOZIMA S. et al.

It may be noted that the reaction of conversion of a carbamate to urea, and in particular of a sulfonylcarbamate to sulfonylurea, can be carried out, for example, at the reflux of a solvent such as, for example, toluene in the presence of the appropriate amine.

It is understood that the reactions described above can be carried out as indicated or else, where appropriate, according to other usual methods known to those skilled in the art.

i) The removal of protective groups, such as, for example, those indicated above, can be carried out under the usual conditions known to those skilled in the art, in particular by acid hydrolysis carried out with an acid such as hydrochloric, benzenesulfonic or para-toluenesulfonic acid, or formic or trifluoroacetic acid, or else by catalytic hydrogenation.

The phthalimido group can be removed with hydrazine.

A list of various protective groups which can be used will for example be found in patent FR 2 499 995.

j) The products described above can, if desired, be the subject of salification reactions, for example with an inorganic or organic acid or with an inorganic or organic base, according to the usual methods known to those skilled in the art.

k) The optional optically active forms of the products described above can be prepared by resolving the racemic mixtures according to the usual methods known to those skilled in the art.

The starting product of formula (II), namely 2,6-dichloropurine, is known and commercially available.

Among the starting products of formulae (III) and (V), some are known and can be obtained commercially or can be prepared according to the usual methods known to those skilled in the art.

Among the commercially available starting products of formulae (III), (V), (XIV), (XV) and (XVI), mention may, for example, be made of the following products: as commercially available products of formula (XIV), mention may be made of trans-1,4-diaminocyclohexane, trans-4-aminocyclohexanol or else benzylamine, para-methoxybenzylamine or para-fluorobenzylamine.

It is also possible in particular to prepare some starting products from commercially available products, for example by subjecting them to one or more of the reactions described above in a) to k), carried out under the conditions also described above.

By way of example, mention may also be made of: examples of products of formula (II) as defined above are given below in the preparation of the examples of the present invention.

The experimental section below gives examples of such starting products.

Finally, a subject of the present invention is, as new industrial products, the compounds of formula (IV) such as in particular the product 6-(1H-benzimidazol-1-yl)-2-chloro-9H-purine.

Illustrations of such reactions defined above are given in the preparation of the examples described below.

The products of formula (I) as defined above, and also their addition salts with acids, exhibit advantageous pharmacological properties.

The products of the present invention as defined above have kinase-inhibiting properties with great selectivity.

Cdks play a central role in initiating, developing and concluding the events of the cell cycle and, thus, cdk-inhibiting molecules are capable of limiting undesired cell proliferations such as those observed in cancers, psoriasis, fungal growth, and growth of parasites (animals, protists): such cdk-inhibiting molecules are thus also capable of intervening in the regulation of neurodegenerative diseases such as Alzheimer's disease.

Kinases which are particularly sensitive to the inhibitory effects of the derivatives of the present invention are in particular cdk1, cdk2, cdk4, cdk5 and cdk7.

The products of the present invention therefore possess antimitotic properties.

The products of the present invention have, in addition to their kinase-specific inhibiting properties, advantageous cellular effects such as antiproliferative properties and in particular effects on apoptosis.

It is known, through studies described in the literature, such as in WO 97/20842, that relationships exist between the cell cycle and apoptosis. Among the pathways leading to apoptosis, some are kinase-dependent.

The products of the present invention are in particular of use for the treatment of tumors.

The products of the invention can thus also increase the therapeutic effects of commonly used antitumor agents.

The products of formula (I) of the present invention therefore have most particularly antimitotic and antineurodegenerative properties.

The products of formula (I) as defined above can therefore be used as tyrosine kinase inhibitors: such tyrosine kinases can belong to diverse families such as, for example, the Src family in which are found in particular Src, Fyn, Lck, Yes, Fgr, Hck and Yrk, or else, for example, the Csk, Btk, Abl, Fak, Jak, Syk, Fps, Zap 70, EGF, PDGF and CSF families. Such a list of protein tyrosine kinases is not exhaustive.

Among these tyrosine kinase proteins, it may be noted that tyrosine kinase proteins associated with receptors, such as, for example, EGF, PDGF or CSF, and cytoplasmic tyrosine kinase proteins, among which in particular Src, Fyn, Lck, Yes, Fgr, Hck and Yrk, or else Csk, Btk, Abl, Fak, Jak, Syk, Fps and Zap 70, are distinguished.

The products of formula (I) as defined above can also be used to inhibit the catalytic (tyrosine kinase) domain of the Src protein, the method consisting in administering, to the patient whose treatment requires inhibition of the catalytic (tyrosine kinase) domain of the Src protein, an inhibitory amount of one or more products of formula (I) as defined above.

The products of formula (I) as defined above are most particularly inhibitors of the Src catalytic domain: such inhibitors are thus in particular capable of inhibiting the adhesion of osteoclasts to the surface of bone and thus bone resorption by osteoclasts.

The bone diseases for which treatment or prevention requires the use of the products of formula (I) as defined above are in particular osteoporosis, hypercalcemia, osteopenia, for example caused by bone metastases, dental disorders, for example periodontal diseases, hyperparathyroidism, periarticular erosions in rhumatoid arthritis, Paget's disease, and immobilization-induced osteopenia. In addition, the products of formula (I) as defined above can be used to relieve, prevent or treat bone disorders which are caused by treatments, by glucocorticoids, therapies associated with the taking of steroids or corticosteroids, or by male or female sex hormone deficiencies.

All these disorders are characterized by bone loss, which is based on a deficiency in balance between bone formation and bone destruction and which can be favorably influenced by inhibiting bone resorption by osteoclasts.

The products of formula (I) as defined above, by virtue of their affinity with the catalytic (tyrosine kinase) domain of Src, can also be used in other therapeutic applications. For example, it is known that platelets and neurones are tissues which also express the Src protein. In addition, since several proteins of this family are mostly expressed in the hematopoietic system, many applications in the treatment of immunity, of infection, of allergy and of autoimmune diseases can be envisioned.

Finally, the products of formula (I) as defined above can also be used to inhibit the catalytic (tyrosine kinase) domain of proteins other than Src, the method consisting in administering, to the patient whose treatment requires inhibition of the catalytic (tyrosine kinase) domain, an inhibitory amount of one or more products of formula (I) as defined above.

Such proteins containing the catalytic (tyrosine kinase) domain, other than Src, can therefore be chosen in particular from Fyn, Lck, Yes, Fgr, Hck, Yrk, Csk, Btk, Abl, Fak, Jak, Syk, Fps, Zap 70, EGF, PDGF and CSF. Such a list of protein tyrosine kinases is not exhaustive.

The products of formula (I) as defined above can also be used to inhibit the serine/threonine kinase catalytic domain in particular among CDKs.

The products of formula (I) as defined above can thus be used in the treatment of diseases such as proliferative diseases, cancer, restenosis, inflammation; allergies or cardiovascular diseases.

The products of the present invention as defined above have protein kinase-inhibiting properties as indicated above and in particular inhibitory properties for CIV1 as defined above.

CIV1s play a central role in entry into the cell cycle via Cdk activation and, thus, the CIV1-inhibiting molecules are capable of limiting undesired cell proliferations such as those observed in fungal growths.

The products of formula (I) of the present invention can therefore have antimitotic properties.

These properties justify their application in therapeutics, and a subject of the invention is particularly, as medicinal products, the products of formula (I) as defined above, said products of formula (I) being in all the possible racemic, enantiomeric and diastereoisomeric isomer forms, and also the pharmaceutically acceptable addition salts with inorganic and organic acids or with inorganic and organic bases of said products of formula (I).

A subject of the invention is more particularly, as medicinal products, the products as defined by formula (Id) as defined above.

A subject of the invention is most particularly, as medicinal products, the products described below in the examples, and in particular the products of formula (I) as defined above, corresponding to the following formulae:

trans-N-[6-(5,6-dichloro-2,3-dihydro-1H-indol-1-yl)-9H-purin-2-yl]-1,4-cyclohexanediamine dihydrochloride
trans-N-[6-(1H-benzimidazol-1-yl)-9H-purin-2-yl]-1,4-cyclohexanediamine dihydrochloride
trans-N-[6-(5,6-dimethyl-1H-benzimidazol-1-yl)-9H-purin-2-yl]-1,4-cyclohexanediamine
trans-N-[6-(5,6-dichloro-1H-benzimidazol-1-yl)-9H-purin-2-yl]-1,4-cyclohexanediamine hydrochloride
trans-N-[6-(5-methoxy-1H-benzimidazol-1-yl)-9H-purin-2-yl]-1,4-cyclohexanediamine dihydrochloride
trans-N-[6-(1H-indol-1-yl)-9H-purin-2-yl]-1,4-cyclohexanediamine dihydrochloride
trans-N-[6-[6-(phenylmethoxy)-1H-benzimidazol-1-yl]-9H-purin-2-yl]-1,4-cyclohexanediamine
trans-N-[6-[5-(phenylmethoxy)-1H-benzimidazol-1-yl]-9H-purin-2-yl]-1,4-cyclohexanediamine
trans-4-[[6-(1H-benzimidazol-1-yl)-9H-purin-2-yl]-amino]cyclohexanol
trans-N-[6-(2,3-dihydro-5-nitro-1H-indol-1-yl)-9H-purin-2-yl]-1,4-cyclohexanediamine dihydrochloride
trans-N-[6-(2,3-dihydro-6-(trifluoromethyl)-1H-indol-1-yl) -9H-purin-2-yl]-1,4-cyclohexanediamine (ex 40)
trans-N-[1-[2-[(4-aminocyclohexyl)amino]-9H-purin-6-yl]-2,3-dihydro-1H-indol-5-yl]-2-thiopheneacetamide (ex 41)
trans-N-[6-(6-nitro-2,3-dihydro-1H-indol-1-yl)-9H-purin-2-yl]-1,4-cyclohexanediamine (ex 44).

The medicinal products, which are the subject of the invention, are, for example, of use, as antimitotics, in cancer chemotherapy or else in the treatment of psoriasis or of parasitic diseases such as those due to protists or to fungi, or else in the treatment of Alzheimer's disease or in the treatment of neuronal apoptosis.

The medicinal products, which are a subject of the invention, are of use in particular in the treatment of diseases due to fungi, such as candidosis, aspergillosis, histoplasmosis and coccidiosis.

The invention extends to the pharmaceutical compositions containing, as active principle, at least one of the medicinal products as defined above.

Such compositions can in particular be useful for treating topical and systemic fungal infections.

The pharmaceutical compositions indicated above can be administered orally, rectally, parenterally or locally by topical application to the skin and the mucous membranes, or by intravenous or intramuscular injection. These compositions may be solid or liquid and may be in all the pharmaceutical forms commonly used in human medicine, such as, for example, simple or sugar-coated tablets, gelatin capsules, granules, suppositories, injectable preparations, ointments, creams, gels, aerosol preparations, vaginal pessaries and gynecological capsules. These compositions are prepared according to the usual methods. The active principle may be incorporated therein in excipients conventionally used in these pharmaceutical compositions, such as talc, gum arabic, lactose, starch, magnesium stearate, cocoa butter, aqueous or nonaqueous vehicles, fatty substances of animal or plant origin, paraffin derivatives, glycols, various wetting agents, dispersing agents or emulsifiers, or preserving agents.

The dosage will be variable depending on the product used, the individual treated and the ailment in question, and can be, for example, from 0.05 to 5 g per day in adults, or preferably from 0.1 to 2 g per day.

A subject of the invention is therefore particularly the pharmaceutical compositions as defined above, which are used as medicinal products.

A subject of the invention is thus in particular the use of the products of formula (I) as defined above, and/or of their pharmaceutically acceptable salts, for preparing medicinal products intended for the prevention or treatment of fungal diseases such as mycoses due to fungi chosen in particular from the fungi defined above.

A subject of the invention is more precisely the use of the products of formula (I) as defined above, and/or of their pharmaceutically acceptable salts, for preparing medicinal products intended for the prevention or treatment of fungal diseases such as in particular candidiasis, aspergillosis, histoplasmosis and coccidiosis.

A subject of the invention is particularly the use of the products of formula (I) as defined above, and/or of their pharmaceutically acceptable salts, for preparing medicinal products intended for the prevention or treatment of diseases caused by *Candida albicans*, and in particular intended for the prevention or treatment of systemic candidiosis.

A subject of the inventin is thus the products of formula (I) as defined above having antifungal properties, as inhibitors of *Candida albicans* CIV1 protein kinases.

A subject of the invention is thus the pharmaceutical compositions containing, as active principle, at least one inhibitor of *Candida albicans* CIV1 protein kinases as defined above.

A subject of the present invention is in particular the use of the compositions as defined above, as antifungal agents.

A subject of the present invention is thus the pharmaceutical compositions as defined above, which are used as antimitotic medicinal products, in particular for cancer chemotherapy or else for the treatment of psoriasis, of parasitic diseases such as those due to fungi or to protists, or of Alzheimer's disease.

A subject of the present invention is thus the pharmaceutical compositions as defined above, which are used as antineurodegenerative, in particular antineuronal apoptosis, medicinal products.

A subject of the present invention is also the use of the products of formula (I) as defined above, and/or of their pharmaceutically acceptable salts, for preparing medicinal products intended for cancer chemotherapy, for the treatment of psoriasis or of parasitic diseases such as those due to fungi or to protists, for the treatment of Alzheimer's disease or for the treatment of neurodegenerative disorders, in particular neuronal apoptosis.

A subject of the present invention is also the use of the products of formula (I) as defined above, and/or of their pharmaceutically acceptable salts as defined above, for preparing medicinal products intended for the prevention or treatment of diseases associated with a disturbance of the secretion and/or of the activity of protein tyrosine kinases and of serine/threonine kinases.

A subject of the present invention is also the use of the products of formula (I) as defined above, and/or of their pharmaceutically acceptable salts, for preparing medicinal products intended for the treatment or prevention of immunity, infection, allergy, and autoimmune diseases.

A subject of the present invention is also the use of the products of formula (I) as defined above, and/or of their pharmaceutically acceptable salts, for preparing medicinal products intended for the treatment or prevention of diseases such as proliferative diseases, cancer, restenosis, inflammation, allergies or cardiovascular diseases.

The present invention also relates to a method for screening antifungal products according to the present invention, which comprises a step in which the activity of a given protein kinase is measured, and then the products having an inhibitory affect on this activity are selected, thus determining the antifungal properties of the products according to the present invention.

The following examples of products of formula (I) according to the present invention illustrate the invention without however limiting it.

EXPERIMENTAL SECTION

Example 1

Trans-N-[6-(5,6-dichloro-2,3-dihydro-1H-indol-1-yl)-9H-purin-2-yl]-1,4-cyclohexanediamine dihydrochloride Stage 1: 2-chloro-6-(2,3-dihydro-1H-indol-1-yl)-9H-purine 189 mg of 2,6-dichloropurine, 4 ml of butanol and 143 mg (1.2 equivalents) of indoline are mixed and brought to a temperature of 80° C. for approximately 17 hours. The mixture is allowed to return to ambient temperature. Partial drying, washing with ethyl ether and drying under vacuum are carried out, and 262 mg of expected product are obtained in the form of beige-colored crystals.

Stage 2: Trans-N-[6-(5,6-dichloro-2,3-dihydro-1H-indol-1-yl)-9H-purin-2-yl]-1,4-cyclohexanediamine dihydrochloride 800 mg of trans-1,4-diaminocyclohexane are brought to its melting temperature (70° C.), 190 mg of product obtained in stage 1 above are added in a single step, and the mixture is then heated at 140° C. for approximately 6 hours.

The mixture is allowed to return to ambient temperature. Purification is carried out by chromatography on silica with an MeOH—NH$_4$OH: 98-2 mixture for eluent. 4 ml of ethanol and 4 ml of HCl-EtOH (hydrochloric acid-ethanol) are added and washing is carried out with ethanol. Drying is carried out under vacuum at 50° C. 67 mg of expected product are obtained.

Example 2

Trans-N-[6-(1H-benzimidazol-1-yl)-9H-purin-2-yl]-1,4-cyclohexanediamine dihydrochloride Stage 1:
6-(1H-benzimidazol-1-yl)-2-chloro-9H-purine The same procedure as in Example 1 is carried out, starting from 1.89 g of 2,6-dichloropurine, 40 ml of butanol and 1.30 g of benzimidazole. 1.1 g of expected product are obtained.

Stage 2: Trans-N-[6-(1H-benzimidazol-1-yl)-9H-purin-2-yl]-1,4-cyclohexanediamine dihydrochloride 2.52 g of trans-1,4-diaminocyclohexane are brought to its melting temperature (70° C.), 865 mg of product obtained in stage 1 above are added, and the mixture is then heated at 140° C. for approximately 5 hours.

The mixture is allowed to return to ambient temperature. Purification is carried out by chromatography on silica with a CH$_2$Cl$_2$-MeOH—NH$_4$OH: 78-20-2 mixture for eluent. 10 ml of ethanol and 6 ml of HCl-EtOH (hydrochloric acid-ethanol) are added. Evaporation to dryness is carried out and a paste is then formed in ethyl ether. This paste is dried under vacuum.

397 mg of expected product are obtained.

Example 3

6-(1H-benzimidazol-1-yl)-9H-purin-2-amine 500 mg of 2-amino-6-purine, 5 ml of butanol and 383 mg of benzimidazole are mixed and brought to a temperature of 90° C. for approximately 48 hours, and then 140° C. for 48 hours. Purification is carried out by chromatography on silica with a CH$_2$Cl$_2$-MeOH—NH$_4$OH: 95-5-0.3 mixture for eluent.

A paste is formed in methanol. 250 mg of expected product are obtained.

Example 4

6-(1H-benzimidazol-1-yl)-N,N-dimethyl-9H-purin-2-amine

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-N,N-dimethyl-9H-purin-2-amine 300 mg of product obtained in stage 1 above are mixed with 3 ml of DMF (dimethylformamide) and 0.17 ml (1.1 equivalents) of TEA (triethylamine). The mixture is heated at 90° C. for 2 hours. The precipitate is filtered off. Purification is carried out by chromatography on silica with a $CH_2Cl_2$-MeOH—$NH_4OH$: 90-9-9 mixture for eluent. 298 mg of expected product are obtained.

Example 5

Trans-N-[6-(5,6-dimethyl-1H-benzimidazol-1-yl)-9H-purin-2-yl]-1,4-cyclohexanediamine Stage 1: 2-chloro-6-(5,6-dimethyl-1H-benzimidazol-1-yl)-9H-purine 283 mg of 2,6-dichloropurine, 5 ml of butanol and 219 mg of 5,6-dimethylbenzimidazole are mixed and brought to a temperature of 100° C. for approximately 17 hours. The mixture is allowed to return to ambient temperature. Partial drying, washing with isopropanol and drying under vacuum at 50° C. are carried out, and 194 mg of expected product are obtained, in the form of cream-colored crystals.

Stage 2: Trans-N-[6-(5,6-dimethyl-1H-benzimidazol-1-yl)-9H-purin-2-yl]-1,4-cyclohexanediamine 570 mg of trans-1,4-diaminocyclohexane are brought to its melting temperature (70° C.), 149 mg of product obtained in stage 1 above are added in a single step, and the mixture is then heated at 140° C. for approximately 18 hours.

The mixture is allowed to return to ambient temperature. Purification is carried out by chromatography on silica with an MeOH—$NH_4OH$: 98-2 mixture for eluent. 40 mg of expected product are obtained, in the form of beige-colored crystals.

Example 6

Ethyl 3-[[6-(1H-benzimidazol-1-yl)-9H-purin-2-yl]amino]benzoate

Stage 1: 6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: ethyl 3-[[6-(1H-benzimidazol-1-yl)-9H-purin-2-yl]amino]benzoate 300 mg of product obtained in stage 1 above are mixed with 0.83 ml (5 equivalents) of ethyl 3-aminobenzoate and 0.166 mg of NaI, and the mixture is then heated at 140° C. for approximately 4 days.

The mixture is allowed to return to ambient temperature and stirring is carried out at ambient temperature for 2 days. Purification is carried out by chromatography on silica with a $CH_2Cl_2$-MeOH—$NH_4OH$ 95-5-0.3 mixture for eluent. 25.2 mg of expected product are obtained.

Example 7

Trans-N-[6-(5-chloro-2,3-dihydro-1H-indol-1-yl)-9H-purin-2-yl]-1,4-cyclohexanediamine Stage 1: 2-chloro-6-(5-chloro-2,3-dihydro-1H-indol-1-yl)-9H-purine The same procedure as in stage 1 of Example 1 is carried out, starting from 756 mg of 2,6-dichloro-purine, 12 ml of butanol and 737 mg of 5-chloro-2,3-dihydro-1H-indole.

The mixture is brought to a temperature of 80° C. for approximately 20 hours.

The mixture is allowed to return to ambient temperature. Partial drying, washing with isopropanol, and drying are carried out. 1.67 g of expected product are thus obtained.

Stage 2: Trans-N-[6-(5-chloro-2,3-dihydro-1H-indol-1-yl)-9H-purin-2-yl]-1,4-cyclohexanediamine The same procedure as in stage 2 of Example 1 is carried out, starting from 1.14 g of trans-1,4-diaminocyclohexane and 306 mg of the product obtained in stage 1 above; the mixture is then heated at 120° C. for approximately 6 hours.

140 mg of expected product are obtained, in the form of beige-colored crystals.

Example 8

Trans-N-[6-(5,6-dichloro-1H-benzimidazol-1-yl)-9H-purin-2-yl]-1,4-cyclohexanediamine hydrochloride Stage 1: 2-chloro-6-(5,6-dichloro-1H-benzimidazol-1-yl)-9H-purine 567 mg of 2,6-dichloropurine, 6 ml of butanol and 617 mg of 5,6-dichlorobenzimidazole are mixed and brought to a temperature of 100° C. for approximately 24 hours. The mixture is allowed to return to ambient temperature. Partial drying, washing with isopropanol and drying under vacuum at 50° C. are carried out, and 548 mg of expected product are obtained, in the form of gray/black-colored crystals.

Stage 2: trans-N-[6-(5,6-dichloro-1H-benzimidazol-1-yl)-9H-purin-2-yl]-1,4-cyclohexanediamine hydrochloride 570 mg of trans-1,4-diaminocyclohexane are brought to its melting temperature (70° C.), 170 mg of product obtained in stage 1 above are added in a single step, and the mixture is then heated at 110° C. for approximately 24 hours. The mixture is allowed to return to ambient temperature. Purification is carried out by chromatography on silica with an MeOH—$NH_4OH$: 98-2 mixture for eluent. The purified product is dissolved in ethanol and HCl-AcOEt (hydrochloric acid-ethyl acetate) is then added. Partial drying and drying under vacuum at 50° C. are carried out. 34 mg of expected product are obtained in the form of brown-colored crystals.

Example 9

6-(1H-benzimidazol-1-yl)-N-(phenylmethyl)-9H-purin-2-amine

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-N-(phenylmethyl)-9H-purin-2-amine 300 mg of product obtained in stage 1 above are mixed with 2 ml of DMSO and 0.27 g (5 equivalents) of n-butylamine, and the mixture is then heated at 120° C. for approximately 48 hours. The mixture is allowed to return to ambient temperature. Purification is carried out by chromatography on silica with a $CH_2Cl_2$-MeOH—$NH_4OH$: 90-9-1 mixture for eluent. Evaporation is carried out and a paste is formed in methylene chloride. 351 mg of expected product are obtained.

Example 10

6-(1H-benzimidazol-1-yl)-N-butyl-9H-purin-2-amine

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-N-butyl-9H-purin-2-amine 200 mg of product obtained in stage 1 above are mixed with 3 ml of DMSO and 0.6 ml (5 equivalents) of benzylamine, and the mixture is then heated at 120° C. for approximately 60 hours. The mixture is allowed to return to ambient temperature. Purification is carried out by chromatography on silica with a $CH_2Cl_2$-MeOH—$NH_4OH$: 90-9-1 mixture for eluent. Evaporation is carried out and a paste is formed in methylene chloride. Partial drying and drying under vacuum at 50° C. are carried out. 105 mg of expected product are obtained.

Example 11

2-[[6-(1H-benzimidazol-1-yl)-9H-purin-2-yl]amino]ethanol

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 2-[[6-(1H-benzimidazol-1-yl)-9H-purin-2-yl]amino]ethanol 210 mg of product obtained in stage 1 above are mixed with 2 ml of DMSO and 0.3 ml of ethanolamine, and the mixture is then heated at 120° C. for approximately 48 hours with stirring. The mixture is allowed to return to ambient temperature. Purification is carried out by chromatography on silica with a $CH_2Cl_2$-MeOH—$NH_4OH$: 90-9-1 mixture for eluent. Evaporation is carried out and a paste is formed in methylene chloride-methanol (5-5). Partial drying and drying under vacuum at 50° C. are carried out. 118 mg of expected product are obtained.

Example 12

6-(1H-benzimidazol-1-yl)-N-methyl-9H-purin-2-amine

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-N-methyl-9H-purin-2-amine 200 mg of product obtained in stage 1 above are mixed with 2 ml of DMSO and 0.115 ml (5 equivalents) of methylamine, and the mixture is then heated at 120° C. for approximately 18 hours. The mixture is allowed to return to ambient temperature. Purification is carried out by chromatography on silica with a $CH_2Cl_2$-MeOH—$NH_4OH$: 90-9-1 mixture for eluent. Evaporation is carried out and a paste is formed in methylene chloride. Partial drying and drying under vacuum at 50° C. are carried out. 190 mg of expected product are obtained.

Example 13

6-(1H-benzimidazol-1-yl)-N-cyclohexyl-9H-purin-2-amine

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-N-cyclohexyl-9H-purin-2-amine 200 mg of product obtained in stage 1 above are mixed with 2 ml of DMSO and 0.42 ml of cyclohexylamine, and the mixture is then heated at 110° C. for approximately 48 hours. The mixture is allowed to return to ambient temperature. Purification is carried out by chromatography on silica with a CH$_2$Cl$_2$-MeOH—NH$_4$OH: 90-9-1 mixture for eluent. 84.7 mg of expected product are obtained.

Example 14

2,2'-[[6-(1H-benzimidazol-1-yl)-9H-purin-2-yl]imino]bisethanol

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 2,2'-[[6-(1H-benzimidazol-1-yl)-9H-purin-2-yl]imino]bisethanol 200 mg of product obtained in stage 1 above are mixed with 3 ml of DMSO and 0.388 mg (5 equivalents) of diethanolamine, and the mixture is then heated at 120° C. for approximately 48 hours. The mixture is allowed to return to ambient temperature. Purification is carried out by chromatography on silica with a CH$_2$Cl$_2$-MeOH—NH$_4$OH: 90-9-1 mixture for eluent. Evaporation is carried out and a paste is formed in methylene chloride. Partial drying and drying under vacuum at 50° C. are carried out. 88.2 mg of expected product are obtained.

Example 15

Trans-N-[6-(5-methoxy-1H-benzimidazol-1-yl)-9H-purin-2-yl]-1,4-cyclohexanediamine dihydrochloride Stage 1: 2-chloro-6-(5-methoxy-1H-benzimidazol-1-yl)-9H-purine 567 mg of 2,6-dichloropurine, 15 ml of butanol and 999 mg of 5-OCH$_3$-benzimidazole are mixed and brought to a temperature of 120° C. for approximately 24 hours. The mixture is allowed to return to ambient temperature. Partial drying, washing with H$_2$Cl$_2$ and drying under vacuum at 50° C. are carried out. The product is taken up in H$_2$O$^+$; 1 ml of NH$_4$OH is added and then extraction is carried out with CH$_2$Cl$_2$ and a saturated aqueous NaCl solution is added. Drying is carried out over sodium sulfate and the product is brought to dryness. 60 mg of expected product are obtained, in the form of white-colored crystals.

Stage 2: Trans-N-[6-(5-methoxy-1H-benzimidazol-1-yl)-9H-purin-2-yl]-1,4-cyclohexanediamine dihydrochloride 969 mg of trans-1,4-diaminocyclohexane are brought to its melting temperature (70° C.), 5100 mg of product obtained in stage 1 above (no name) and 10 ml of DMSO are added in a single step, and the mixture is then heated at 120° C. for approximately 72 hours. The mixture is allowed to return to ambient temperature. Purification is carried out by chromatography on silica with an MeOH—NH$_4$OH: 98-2 mixture for eluent. The purified product is dissolved in ethanol and HCl-AcOEt is then added. Partial drying and drying under vacuum at 60° C. are carried out. Purification is carried out by chromatography on silica with a CH$_2$Cl$_2$-MeOH—NH$_4$OH: 75-23-2 mixture for eluent. 258 mg of expected product are obtained, in the form of beige-colored crystals.

Example 16

Trans-N-[6-(1H-indol-1-yl)-9H-purin-2-yl]-1,4-cyclohexanediamine dihydrochloride Stage 1: 2-chloro-6-(1H-indol-1-yl)-9H-purine 236 mg of product obtained in stage 1 of Example 1 in 20 ml of dioxane are heated over siliparite with 227 mg of DDQ (dichlorodicyanobenzoquinone), for 60 hours at 80° C. The dioxane is evaporated off and then purification is carried out by chromatography on silica with a CH$_2$Cl$_2$-MeOH: 95-5 mixture for eluent. 142 mg of expected product are obtained, in the form of beige-colored crystals.

Stage 2: Trans-N-[6-(1H-indol-1-yl)-9H-purin-2-yl]-1,4-cyclohexanediamine dihydrochloride 1.31 g of trans-1,4-diaminocyclohexane are brought to its melting temperature (70° C.), 310 mg of product obtained in stage 1 above are added, and the mixture is then heated at 140° C. for approximately 18 hours. The mixture is allowed to return to ambient temperature. Purification is carried out by chromatography on silica with an MeOH—NH$_4$OH: 98-2 mixture for eluent. 4 ml of ethanol and then 2 ml of hydrochloric acid-ethanol (8N) are added. Partial drying followed by washing with ethanol are carried out. Drying is carried out under vacuum. 23 mg of expected product are obtained, in the form of beige-colored crystals.

Example 17

6-(1H-benzimidazol-1-yl)-N-phenyl-9H-purin-2-amine

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-N-phenyl-9H-purin-2-amine 300 mg of product obtained in stage 1 above are mixed with 0.52 ml of aniline and the mixture is then heated at 140° C. for approximately 72 hours. The mixture is allowed to return to ambient temperature for 48 hours. A paste is formed in methylene chloride and partial drying is carried out. 48 mg of expected product are obtained.

Example 18

2-[[6-(1H-benzimidazol-1-yl)-9H-purin-2-yl]amino]-1,3-propanediol

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 2-[[6-(1H-benzimidazol-1-yl)-9H-purin-2-yl]-amino]-1,3-propanediol 200 mg of product obtained in stage 1 above are mixed with 3 ml of DMSO and 336 mg (5 equivalents) of 2-amino-1,3-propanediol, and the mixture is then heated at 120° C. for approximately 72 hours. The mixture is allowed to return to ambient temperature. Purification is carried out by chromatography on silica with a $CH_2Cl_2$-MeOH—$NH_4OH$: 90-9-1 mixture for eluent. Evaporation is carried out and a paste is formed in methylene chloride-methanol: 50-50. Partial drying and drying under vacuum at 50° C. are carried out. 91.4 mg of expected product are obtained.

Example 19

Trans-N-[6-[6-(phenylmethoxy)-1H-benzimidazol-1-yl]-9H-purin-2-yl]-1,4-cyclohexanediamine Stage 1: 2,6-dichloro-9-[[2-(trimethylsilyl)ethoxy]-methyl]-9H-purine 945 mg of 2,6-dichloropurine, 15 ml of DMF (dimethylformamide) and 288 mg of NaH are mixed and left at ambient temperature for 2 hours. 1.06 ml of 2-chloromethoxyethyltrimethylsilane are then added. The mixture is stirred for 18 hours at ambient temperature. The DMF is evaporated off. The product is taken up in methylene chloride. Washing is carried out with a saturated sodium bicarbonate solution and then once with $H_2O$ and, finally, with a saturated NaCl solution. Drying over $Na_2SO_4$ and evaporation to dryness are carried out. Purification is carried out by chromatography on silica with a $CHCl_3$-AcOEt: 5-5 mixture for eluent. 876 mg of expected product are obtained, in the form of a yellow-colored oil.

Stage 2: 2-chloro-6-[6-(phenylmethoxy)-1H-benzimidazol-1-yl]-9-[[2-(trimethylsilyl)ethoxy]methyl]-9H-purine 860 mg of product obtained in stage 1 above are mixed with 605 mg of 5-(phenylmethoxy)-1H-benzimidazole (benzyl ether in the 5-position of benzimidazole) and 15 ml of butanol. The mixture is heated at 120° C. for 24 hours. Partial drying, washing with $H_2O$ and then drying under vacuum at 50° C. are carried out. 667 mg of 2-chloro-6-[6-(phenylmethoxy)-1H-benzimidazol-1-yl]-9-[[2-(trimethylsilyl)ethoxy]methyl]-9H-purine are obtained, in the form of beige-colored crystals.

Stage 3: Trans-N-[6-[6-(phenylmethoxy)-1H-benzimidazol-1-yl]-9H-purin-2-yl]-1,4-cyclohexanediamine 1 g of trans-1,4-diaminocyclohexane is brought to its melting temperature (70° C.), 15 ml of DMSO and 530 mg of product obtained in stage 1 above are added, and the mixture is then heated at 120° C. for approximately 21 hours. Purification is carried out by chromatography on silica with a $CH_2Cl_2$-MeOH—$NH_4OH$: 85-13.5-1.5 mixture for eluent. 38 mg of expected product are obtained, in the form of beige-colored crystals.

Example 20

Trans-N-[6-[5-(phenylmethoxy)-1H-benzimidazol-1-yl]-9H-purin-2-yl]-1,4-cyclohexanediamine Stage 1: 2,6-dichloro-9-[[2-(trimethylsilyl)ethoxy]-methyl]-9H-purine 945 mg of 2,6-dichloropurine, 15 ml of DMF (dimethylformamide) and 288 mg of NaH are mixed and left at ambient temperature for 2 hours. 1.06 ml of 2-chloromethoxyethyltrimethylsilane are then added. Stirring is carried out for 18 hours at ambient temperature. The DMF is evaporated off. The product is taken up in methylene chloride. Washing is carried out with a saturated sodium bicarbonae solution, then once with $H_2O$ and, finally, with a saturated NaCl solution. Drying over $Na_2SO_4$ and evaporation to dryness are carried out. Purification is carried out by chromatography on silica with a $CHCl_3$-AcOEt: 5-5 mixture for eluent. 876 mg of expected product are obtained, in the form of a yellow-colored oil.

Stage 2: 2-chloro-6-[5-(phenylmethoxy)-1H-benzimidazol-1-yl]-9-[[2-(trimethylsilyl)ethoxy]-methyl]-9H-purine 860 mg of product obtained in stage 1 above are mixed with 605 mg of 5-(phenylmethoxy)-1H-benzimidazole (benzyl ether in the 5-position of benzimidazole) and 15 ml of butanol. The mixture is heated at 120° C. for 24 hours. Partial drying, washing with $H_2O$ and then drying under vacuum at 50° C. are carried out. 667 mg of 2-chloro-6-[5-(phenylmethoxy)-1H-benzimidazol-1-yl]-9-[[2-(trimethylsilyl)ethoxy]methyl]-9H-purine are obtained, in the form of beige-colored crystals.

Stage 3: Trans-N-[6-[5-(phenylmethoxy)-1H-benzimidazol-1-yl]-9H-purin-2-yl]-1,4-cyclohexanediamine 1 g of trans-1,4-diaminocyclohexane is brought to its melting temperature (70° C.), 15 ml of DMSO and 530 mg of product obtained in stage 1 above are added, and the mixture is then heated at 120° C. for approximately 21 hours. Purification is carried out by chromatography on silica with a $CH_2Cl_2$-MeOH—$NH_4OH$: 85-13.5-1.5 mixture for eluent. 39 mg of expected product are obtained, in the form of beige-colored crystals.

Example 21

Trans-N-[6-(1H-benzimidazol-1-yl)-9H-purin-2-yl]-1,2-cyclohexanediamine dihydrochloride

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: Trans-N-[6-(1H-benzimidazol-1-yl)-9H-purin-2-yl]-1,2-cyclohexanediamine dihydrochloride 200 mg of product obtained in stage 1 above are mixed with 3 ml of DMSO and 420 mg (5 equivalents) of (1S,2S)-(−)-1,2-diaminocyclohexane, and the mixture is then heated at 120° C. for approximately 4 days. The mixture is allowed to return to ambient temperature. Purification is carried out by chromatography on silica with a $CH_2Cl_2$-MeOH—$NH_4OH$: 95-5-0.33 mixture for eluent. 4 ml of ethanol and 4 ml of HCl-EtOH (hydrochloric acid-ethanol) are added. Evaporation to dryness is carried out and a paste is then formed in ethyl ether. Drying is carried out under vacuum. 116 mg of expected product are obtained.

Example 22

1,1-dimethylethyl [1-[6-(1H-benzimidazol-1-yl)-9H-purin-2-yl]-4-piperidinyl]carbamate

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 1,1-dimethylethyl [1-[6-(1H-benzimidazol-1-yl)-9H-purin-2-yl]-4-piperidinyl]carbamate 200 mg of product obtained in stage 1 above are mixed with 3 ml of DMSO and 740 mg (5 equivalents) of Boc-4-aminopiperidine, and the mixture is then heated at 120° C. for approximately 4 hours. The mixture is allowed to return to ambient temperature. Purification is carried out by chromatography on silica with a $CH_2Cl_2$-MeOH—$NH_4OH$: 90-9-1 mixture for eluent. Evaporation to dryness is carried out and then a paste is formed in dichloromethane. Drying is carried out under vacuum. 252 mg of expected product are obtained.

Example 23

Cis-N-[6-(1H-benzimidazol-1-yl)-9H-purin-2-yl]-1,2-cyclohexanediamine dihydrochloride

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: Cis-N-[6-(1H-benzimidazol-1-yl)-9H-purin-2-yl]-1,2-cyclohexanediamine dihydrochloride 200 mg of product obtained in stage 1 above are mixed with 3 ml of DMSO and 0.5 ml (5 equivalents) of cis-1,2-diaminocyclohexane, and the mixture is then heated at 120° C. for approximately 3 days. The mixture is allowed to return to ambient temperature. Purification is carried out by chromatography on silica with a $CH_2Cl_2$-MeOH—$NH_4OH$: 85-15-1.5 mixture for eluent. 3 ml of ethanol and 3 ml of HCl-EtOH (hydrochloric acid-ethanol) are added. 34.3 mg of expected product are obtained.

Example 24

Trans-4-[[6-(1H-benzimidazol-1-yl)-9H-purin-2-yl]amino]cyclohexanol

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: Trans-4-[[6-(1H-benzimidazol-1-yl)-9H-purin-2-yl]amino]cyclohexanol 200 mg of product obtained in stage 1 above are mixed with 3 ml of DMSO and 586 mg (5 equivalents) of trans-4-aminocyclohexanol, and the mixture is then heated at 120° C. for approximately 4 days. The mixture is allowed to return to ambient temperature. Purification is carried out by chromatography on silica with a $CH_2Cl_2$-MeOH—$NH_4OH$: 85-15-1.5 mixture for eluent. 45 mg of expected product are obtained.

Example 25

1-[6-(1H-benzimidazol-1-yl)-9H-purin-2-yl]-4-piperidinamine bis(trifluoroacetate)

100 mg of product obtained in Example 22 are mixed with 3 ml of methylene chloride and 1.5 ml of trifluoroacetic acid containing 10% of anisole. The mixture is stirred at ambient temperature for 5 hours. It is concentrated to dryness and co-evaporation with toluene and then with methylene chloride is carried out. Purification is carried out by chromatography on silica with a $CH_2Cl_2$-MeOH—$NH_4OH$: 90-9-1 mixture for eluent. 128 mg of expected product are obtained.

Example 26

Trans-N-[6-(2-methyl-1H-indol-1-yl)-9H-purin-2-yl]-1,4-cyclohexanediamine dihydrochloride

Stage 1: 6-(2-methyl-1H-indol-1-yl)-2-chloro-9H-purine

The same procedure as in stage 1 of Example 1 is carried out, mixing 189 mg of 2,6-dichloropurine, 5 ml of butanol and 0.16 g of 2-methylindoline. The mixture is heated at 130° C. for approximately 1 hour and allowed to return to ambient temperature. Partial drying is carried out, followed by washing with isopropanol. The product is dried and 174 mg of expected product are thus obtained.

Stage 2: Trans-N-[6-(2-methyl-1H-indol-1-yl)-9H-purin-2-yl]-1,4-cyclohexanediamine dihydrochloride The same procedure as in stage 2 of Example 1 is carried out, starting from 638 mg of trans-1,4-diamino-cyclohexane and 161 mg of the product obtained in stage 1 above, and the mixture is heated at 120° C. for 29 hours. Purification is carried out on silica with MeOH—NH$_4$OH: 98-2 for eluent, and 190 mg of product are thus obtained, in the form of a brown-colored resin, the product is dissolved in ethanol and HCl-AcOEt are added, the hydrochloride precipitates, 3 ml of AcOEt are added, and partial drying and drying under vacuum at 50° C. are carried out.

222 mg of the expected product are thus obtained, in the form of beige-colored crystals.

Example 27

(2S)-2-[[6-(1H-benzimidazol-1-yl)-9H-purin-2-yl]amino]-1-butanol

Stage 1: 6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: (2S)-2-[[6-(1H-benzimidazol-1-yl)-9H-purin-2-yl]amino]-1-butanol 200 mg of product obtained in stage 1 above are mixed with 3 ml of DMSO and 350 μl (5 equivalents) of (+/−)-2-amino-1-butanol, and the mixture is then heated at 120° C. for approximately 2 days. The mixture is allowed to return to ambient temperature. Purification is carried out by chromatography on silica with a CH$_2$Cl$_2$-MeOH—NH$_4$OH: 95-5-0.3 mixture for eluent. 40 mg of expected product are obtained.

Example 28

6-(1H-benzimidazol-1-yl)-N-[(tetrahydro-2H-pyran-4-yl)methyl]-9H-purin-2-amine

Stage 1: 6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-N-[(tetrahydro-2H-pyran-4-yl)methyl]-9H-purin-2-amine 250 mg of product obtained in stage 1 above are mixed with 3 ml of DMSO and 531 mg μl of 4-aminomethyl-tetrahydropyran, and the mixture is then heated at 120° C. for approximately 2 days. The mixture is allowed to return to ambient temperature. Purification is carried out by chromatography on silica with a CH$_2$Cl$_2$-MeOH—NH$_4$OH: 90-9-1 mixture for eluent. 142 mg of expected product are obtained.

Example 29

Trans-N-[6-(2-methyl-1H-indol-1-yl)-9H-purin-2-yl]-1,4-cyclohexanediamine

Stage 1: 6-(2-methyl-1H-indol-1-yl)-2-chloro-9H-purine

The same procedure as in stage 1 of Example 1 is carried out, mixing 378 mg of 2,6-dichloropurine, 10 ml of butanol and 0.32 of dimethylindoline. The mixture is heated at 100° C. for approximately 5 hours and allowed to return to ambient temperature. Partial drying and washing with isopropanol are carried out. The product is dried and 423 mg of expected product are thus obtained.

Stage 2: 6-(2-methyl-1H-indol-1-yl)-2-chloro-1H-purine 140 mg of product obtained in stage 1 above are mixed with 170 mg of DDQ (dichlorodicyanobenzoquinone) and 5 ml of dioxane. The mixture is brought to 80-90° C. and then allowed to return to ambient temperature. Filtration, rinsing and drying are carried out. Purification is carried on silica with CHCl$_3$-EtOH-AcOEt: 90-5-5 for eluent. 170 mg of the expected product are thus obtained.

Stage 3: Trans-N-[6-(2-methyl-1H-indol-1-yl)-9H-purin-2-yl]-1,4-cyclohexanediamine The same procedure as in stage 2 of Example 1 is carried out, starting from 684 mg of trans-1,4-diaminocyclohexane and 166 mg of the product obtained in stage 2 above, and the mixture is heated at 140° C. for 6 hours. Purification is carried out on silica with MeOH—NH$_4$OH: 98-2 for eluent, and 51 mg of expected product are thus obtained, in the form of beige-colored crystals.

Example 30

Trans-N-[6-(2,3-dihydro-5-nitro-1H-indol-1-yl)-9H-purin-2-yl]-1,4-cyclohexanediamine dihydrochloride

Stage 1: 2-chloro-6-(2,3-dihydro-5-nitro-1H-indol-1-yl)-9H-purine 567 mg of 2,6-dichloropurine, 10 ml of butanol and 590 mg of 5-nitroindole are mixed. The mixture is heated to 80° C. for approximately 17 hours and allowed to return to ambient temperature. Purification is carried out by chromatography on silica with a CHCl$_3$-ethanol: 95-5 mixture for eluent.

834 mg of expected product are thus obtained, in the form of yellowish-colored crystals.

Stage 2: Trans-N-[6-(2,3-dihydro-5-nitro-1H-indol-1-yl)-9H-purin-2-yl]-1,4-cyclohexanediamine dihydrochloride 421 mg of the product obtained in stage 1 above are mixed with 1.14 g of trans-1,4-diaminocyclohexane and 10 ml of DMSO. The mixture is heated at 120° C. for approximately 29 hours. Drying under vacuum at 50° C. is carried out and the dry product is purified by chromatography on silica with a $CH_2Cl_2$-MeOH—$NH_4OH$: 85-13.5-1.5 mixture for eluent. A paste is formed in ethanol and 2 ml of HCl-ethanol are then added. Drying is carried out under vacuum.

113 mg of expected product are thus obtained, in the form of mustard yellow-colored crystals.

Example 31

1,1-dimethylethyl 4-[[[6-(1H-benzimidazol-1-yl)-9H-purin-2-yl]amino]methyl]-1-piperidine carboxylate Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 1,1-dimethylethyl 4-[[[6-(1H-benzimidazol-1-yl)-9H-purin-2-yl]amino]methyl]-1-piperidine carboxylate 200 mg of product obtained in stage 1 above are mixed with 5 ml of DMSO and 790 mg (5 equivalents) of 4-aminomethyl-N-Boc-piperidine, and the mixture is then heated at 100° C. for approximately 3 days. The mixture is allowed to return to ambient temperature. The DMSO is concentrated to dryness and the dry product is taken up in $CH_2Cl_2$. Purification is carried out by chromatography on silica with a $CH_2Cl_2$-MeOH—$NH_4OH$: 95-5-0.33 mixture for eluent. 56 mg of expected product are thus obtained.

Example 32

Trans-N-[6-(5-bromo-2,3-dihydro-1H-indol-1-yl)-9H-purin-2-yl]-1,4-cyclohexanediamine Stage 1: 6-(5-bromo-2,3-dihydro-9H-indol-1-yl)-2-chloro-9H-purine The same procedure as in stage 1 of Example 7 is carried out, using 950 mg of 5-bromo-2,3-dihydro-1H-indole in place of 737 mg of 5-chloro-2,3-dihydro-1H-indole. 1.32 g of expected product are thus obtained.

Stage 2: Trans-N-[6-(5-bromo-2,3-dihydro-1H-indol-1-yl)-9H-purin-2-yl]-1,4-cyclohexanediamine The same procedure as in stage 2 of Example 7 is carried out, using 350 mg of the product obtained in stage 1 above instead of 306 mg of the product obtained in stage 1 of Example 7. 35 mg of expected product are obtained, in the form of brown-colored crystals.

Example 33

6-(1H-benzimidazol-1-yl)-2-(4-morpholinyl)-9H-purine dihydrochloride

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: 6-(1H-benzimidazol-1-yl)-2-(4-morpholinyl)-9H-purine dihydrochloride 230 mg of product obtained in stage 1 above are mixed with 3 ml of DMSO and 370 mg (5 equivalents) of morpholine, and the mixture is then heated at 120° C. for approximately 16 hours. The mixture is allowed to return to ambient temperature. The DMSO is concentrated to dryness. A paste is formed in $CH_2Cl_2$ (methylene chloride). Drying is carried out under vacuum. The dry product is taken up in 5 ml of HCl (8M) and 10 ml of ethanol and concentrated to dryness, and 209 mg of expected product are obtained.

Example 34

(2S)-1-[6-(1H-benzimidazol-1-yl)-9H-purin-2-yl]-2-pyrrolidinemethanol

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80° C. for approximately 17 hours. The mixture is allowed to return to ambient temperature. Partial drying, washing with ethyl ether and drying under vacuum are carried out, and 3 g of expected product are obtained.

Stage 2: (2S)-1-[6-(1H-benzimidazol-1-yl)-9H-purin-2-yl]-2-pyrrolidinemethanol 250 mg of product obtained in stage 1 above are mixed with 2 ml of DMSO and 470 mg of (S)-(+)-2-pyrrolidinemethanol. The mixture is then heated at 110° C. for approximately 16 hours. The mixture is allowed to return to ambient temperature. A paste is formed in $CH_2Cl_2$ (methylene chloride). Drying is carried out under vacuum. 200 mg of expected product are obtained.

Example 35

(2R)-1-[6-(1H-benzimidazol-1-yl)-9H-purin-2-yl]-2-pyrrolidinemethanol

Stage 1:
6-(1H-benzimidazol-1-yl)-2-chloro-9H-purine 8 g of 2,6-dichloropurine, 150 ml of butanol and 5.5 g of benzimidazole are mixed and brought to a temperature of 80°

C. for approximately 17 hours. The mixture is allowed to return to ambient temperature. Partial drying, washing with ethyl ether and drying under vacuum are carried out, and 3 g of expected product are obtained.

Stage 2: (2R)-1-[6-(1H-benzimidazol-1-yl)-9H-purin-2-yl]-2-pyrrolidinemethanol 250 mg of product obtained in stage 1 above are mixed with 2 ml of DMSO and 400 ml (4 equivalents) of (R)-(−)-2-pyrrolidinemethanol, and the mixture is then heated at 120° C. for approximately 5 hours. The mixture is allowed to return to ambient temperature. The DMSO is concentrated to dryness and the dry product is taken up in $CH_2Cl_2$, then partial drying is carried out. 258 mg of expected product are obtained.

Example 36

6-(1H-benzimidazol-1-yl)-N-(4-piperidinyl-methyl)-9H-purin -2-amine bis(trifluoroacetate)

35 mg of the product of Example 31 are mixed with 1 ml of $CH_2Cl_2$ and 0.5 ml of TFA containing 10% of anisole. The mixture is left to stir for 2 hours at ambient temperature, followed by concentrating to dryness in the presence of toluene and of $CH_2Cl_2$. 40 mg of expected product are thus obtained.

Example 37

Trans-1-[2-[(4-aminocyclohexyl)amino]-9H-purin-6-yl]-2,3-dihydro-N,N-dimethyl-1H-indole-5-sulfonamide dihydrochloride Stage 1: 1-(2-chloro-9H-purin-6-yl)-2,3-dihydro-N,N-dimethyl-9H-indole-5-sulfonamide The same procedure as in stage 1 of Example 7 is carried out, using 1.08 g of 2,3-dihydro-N,N-dimethyl-1H-indole-5-sulfonamide in place of 737 mg of 5-chloro-2,3-dihydro -1H-indole. The mixture is brought to a temperature of 80° C. for approximately 20 hours. 1.628 g of expected product are thus obtained.

Stage 2: Trans-1-[2-[(4-aminocyclohexyl)amino]-9H-purin-6-yl]-2,3-dihydro-N,N-dimethyl-1H-indole-5-sulfonamide dihydrochloride The same procedure as in stage 2 of Example 7 is carried out, using 379 mg of the product obtained in stage 1 above in place of 306 mg of the product obtained in stage 1 of Example 7.

150 mg of expected product are obtained, in the form of cream-colored crystals.

Example 38

Trans-N-[6-(5-fluoro-2,3-dihydro-1H-indol-1-yl)-9H-purin-2-yl]-1,4-cyclohexanediamine dihydrochloride Stage 1: 2-chloro-6-(5-fluoro-2,3-dihydro-1H-indol-1-yl)-9H-purine The same procedure as in stage 1 of Example 7 is carried out, using 658 mg of 5-fluoro-2,3-dihydro-1H-indole instead of 737 mg of 5-chloro-2,3-dihydro-1H-indole. 1.088 g of expected product are thus obtained.

Stage 2: Trans-N-[6-(5-fluoro-2,3-dihydro-1H-indol-1-yl)-9H-purin-2-yl]-1,4-cyclohexanediamine dihydrochloride The same procedure as in stage 2 of Example 7 is carried out, using 290 mg of the product obtained in stage 1 above instead of 306 mg of the product obtained in stage 1 of Example 7.

87 mg of expected product are obtained, in the form of beige-colored crystals.

| | Nomenclature | Examples |
|---|---|---|
| | Trans-1-[1-[2-[(4-aminocyclohexyl)amina]-9H-purin-6-yl]-2,3-dihydro-1H-indol-5-yl]ethanone | example 39 840694 |
| | Trans-N-[6-[2,3-dihydro-6-(trifluoromethyl)-1H-indol-1-yl)-9H-purin-2-yl]-1,4-cyclohexanediamine | example 40 840783 |

-continued

| | Nomenclature | Examples |
|---|---|---|
| 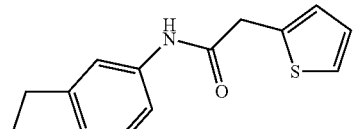 | Trans-N-[1-[2-[(4-aminocyclohexyl)amino]-9H-purin-6-yl]-2,3-dihydro-1H-indol-5-yl]-2-thiopheneacetamide | example 41 A003065673 |
| 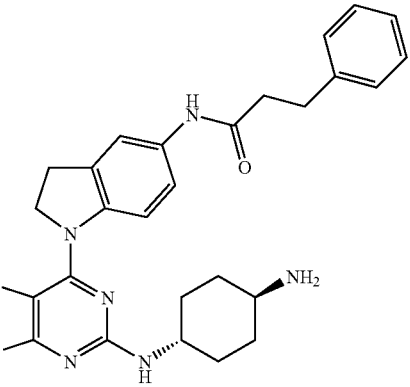 | Trans-N-[1-[2-[(4-aminocyclohexyl) amino]-9H-purin-6-yl]-2,3-dihydro-1H-indol-5-yl]benzenepropanamide | example 42 A003065674 |
| 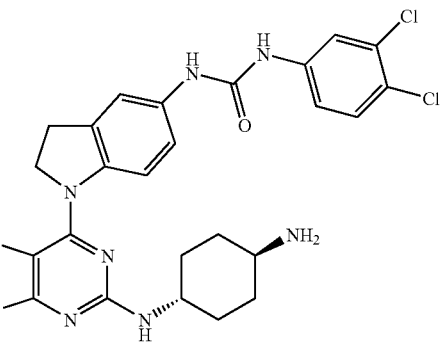 | Trans-N-[1-[2-[(4-aminocyclohexyl) amino]-9H-purin-6-yl]-2,3-dihydro-1H-indol-5-yl]-dichlorophenyl) urea | example 43 A003066533 |
| 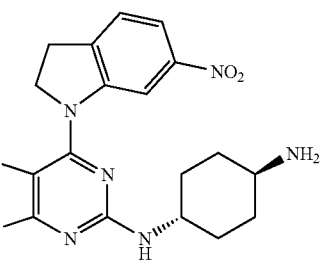 | Trans-N-[6-(6-nitro-2,3-dihydro-1H-indol-1-yl)-9H-purin-2-yl]-1,4-cyclohexanediamine | example 44 A003091244 |

| | Nomenclature | Examples |
|---|---|---|
| [structure] | Trans-N-[1-[2-[(4-aminocyclohexyl)amino]-9H-purin-6-yl]-2,3-dihydro-1H-indol-5-yl]-(dimethylamino)phenylurea | example 45<br>A003066534 |
| [structure] | Trans-N-116-(5-amino-2,3-dihydro-1H-indol-1-yl)-9H-purin-2-yl]-1,4-cyclohexanediamine | example 46<br>A003091245 |

Example 39

Trans-1-[1-[2-[(4-aminocyclohexyl)amino]-9H-purin-6-yl]-2,3-dihydro-1H-indol-5-yl]ethanone Stage 1: 2-chloro-1-[1-(9H-purin-6-yl)-2,3-dihydro-1H-indol-5-yl]ethanone 1.10 g of 2,6-dichloropurine, 12 ml of butanol and 1.13 g of acetylindoline are mixed and brought to a temperature of 90° C. for approximately 3.5 hours. The mixture is allowed to return to ambient temperature. Partial drying, washing with ethyl ether and drying under vacuum are carried out, and 1.94 g of expected product are obtained.

Stage 2: Trans-1-[1-[2-[(4-aminocyclohexyl)amino]-9H-purin-6-yl]-2,3-dihydro-1H-indol-5-yl]ethanone 1.88 g of product obtained in stage 1 above are mixed with 4.8 g of trans-1,4-diaminocyclohexane, and the mixture is then heated at 140° C. for approximately 72 hours. The mixture is allowed to return to ambient temperature for 48 hours. A paste is formed in water, and drying is carried out under vacuum at 50° C. 2.7 g of expected product are obtained, in the form of a beige powder.

Example 40

Trans-N-[6-[2,3-dihydro-6-(trifluoro-methyl)-1H-indol-1-yl)-9H-purin-2-yl]-1,4-cyclohexanediamine Stage 1: 2-chloro-6-[2,3-dihydro-6-(trifluoromethyl)-1H-indol-1-yl]-9H-purine 756 mg of 2,6-dichloropurine, 8 ml of butanol and 897 mg of 6-(trifluoromethyl)indoline are mixed and brought to a temperature of 90° C. for approximately 23 hours. The mixture is allowed to return to ambient temperature. Partial drying, washing with ethyl ether and drying under vacuum at 50° C. are carried out, and 1.256 g of expected product are obtained, in the form of beige crystals.

Stage 2: Trans-N-[6-[2,3-dihydro-6-(trifluoromethyl)-1H-indol-1-yl]-9H-purin-2-yl]-1,4-cyclohexanediamine 340 mg of product obtained in stage 1 above are mixed with 800 mg of trans-1,4-diaminocyclohexane, and the mixture is then heated at 140° C. for approximately 8 hours. The mixture is allowed to return to ambient temperature. Purification is carried out by chromatography on silica with a CH2Cl2-MeOH—NH4OH: 85-15-1.5 mixture for eluent. 275 mg of product are obtained and a paste is formed in HCl/ethanol: 50-50. Partial drying and drying under vacuum at 50° C. are carried out. 244 mg of expected product are obtained.

Example 41

Trans-N-[1-[2-[(4-aminocyclohexyl)amino]-9H-purin -6-yl]-2,3-dihydro-1H-indol-5-yl]-2-thiophene-acetamide Stage 1: 2-chloro-6-(2,3-dihydro-5-nitro-1H-indol-1-yl)-9H-purine 37.8 g of 2,6-dichloropurine, 700 ml of butanol and 32.8 g of 5-nitroindoline are mixed and brought to a temperature of 90° C. for approximately 3 days. The mixture is allowed to return to ambient temperature. Partial drying, washing with ethyl ether and drying under vacuum at 50° C. are carried out and 57.3 g of expected product are obtained, in the form of beige crystals.

Stage 2: trans-N-[6-(2,3-dihydro-5-nitro-1H-indol-1-yl)-9H-purin-2-yl]-1,4-cyclohexanediamine 56 g of product obtained in stage 1 above are mixed with 140 g of trans-1,4-diaminocyclohexane, and the mixture is then heated at 140° C. for approximately 55 hours. The mixture is allowed to return to ambient temperature. Purification is carried out by chromatography on silica with a CH2Cl2-MeOH—NH$_4$OH: 85-15-1.5 mixture for eluent. 19.7 g of product are recovered.

Stage 3: 1,1-dimethylethyl trans-6-(2,3-dihydro-5-nitro-1H-indol-1-yl)-2-[[4-[[(1,1-dimethylethoxy)carbonyl]amino]cyclohexyl]amino]-9H-purine-9-carboxylate 9.46 g of product obtained in stage 2 above are mixed with 160 ml of chloroform and 2.4 ml of triethylamine. The mixture is cooled to 0° C., 31.43 g of BoC$_2$O are then added in a single step, and the mixture is left at 0° C. for 10 minutes and then brought to reflux for 3 hours. The mixture is allowed to return to ambient temperature, 70 ml of water are added, and the mixture is then extracted with 150 ml of dichloromethane. The organic phase is washed with 70 ml of saturated aqueous NaCl solution, dried over sodium sulfate, filtered, and evaporated to dryness. 12.92 g of expected product are thus obtained.

Stage 4: 1,1-dimethylethyl trans-6-(5-amino-2,3-dihydro-1H-indol-1-yl)-2-[[4-[[(1,1-dimethylethoxy)-carbonyl]amino]cyclohexyl]amino]-9H-purine-9-carboxylate 12.65 g of product obtained in stage 3 above in 130 ml of methanol are introduced into a round-bottomed hydrogenation flask; 500 mg of Pd/C are added and the mixture is stirred under a pressure of 1400 mbar of hydrogen for 12 hours. The mixture is filtered over clarcel and the solvent is then evaporated off. The residue is chromatographed on 600 g of silica, with 60/40 dichloromethane/ethyl acetate as eluent.

6 g of expected product are thus obtained.

Stage 5: 1,1-dimethylethyl trans-6-[2,3-dihydro-5-[(2-thienylacetyl)amino]-1H-indol-1-yl]-2-[[4-[[(1,1-dimethylethoxy)carbonyl]amino]cyclohexyl]amino]-9H-purine-9-carboxylate 40 mg of product obtained in stage 4 are mixed with 11.4 mg of 2-thiopheneacetyl chloride, 25 µl of diisopropylethylamine and 2 ml of dichloromethane. The mixture is stirred for 1 hour at ambient temperature, and then washing with brine, drying over magnesium sulfate and evaporation to dryness are carried out.

Stage 6: Trans-N-[1-[2-[(4-aminocyclohexyl)amino]-9H-purin-6-yl]-2,3-dihydro-1H-indol-5-yl]-2-thiophene-acetamide The product obtained in stage 5 is dissolved in 2 ml of methanol. 2 ml of a 2N solution of hydrochloric acid in methanol are added. Stirring is carried out for 48 hours at ambient temperature, followed by evaporation to dryness. The residue is chromatographed on an Xterra LCMSprep column, eluting with acetonitrile/ammonium hydrogen carbonate buffer at 0.2% as a gradient. 6 mg of expected product, example 41, are thus recovered.

Example 42

Trans-N-[1-[2-[(4-aminocyclohexyl)amino]-9H-purin-6-yl]-2,3-dihydro-1H-indol-5-yl]benzenepropanamide

Stage 1: 1,1-dimethylethyl trans-6-[2,3-dihydro-5-[(1-oxo-3-phenylpropyl)amino]-1H-indol-1-yl]-2-[[4-[[(1,1-dimethylethoxy)carbonyl]amino]cyclohexyl]amino]-9H-purine-9-carboxylate 40 mg of product obtained in stage 4 of example 41 are mixed with 11.97 mg of hydrocinnamoyl chloride, 25 µl of diisopropylethylamine and 2 ml of dichloromethane. Stirring is carried out for 1 hour at ambient temperature, followed by washing with brine, drying over magnesium sulfate and evaporation to dryness.

Stage 2: Trans-N-[1-[2-[(4-aminocyclohexyl)amino]-9H-purin-6-yl]-2,3-dihydro-1H-indol-5-yl]benzenepropanamide The product obtained in stage 1 is dissolved in 2 ml of methanol. 2 ml of a 2N solution of hydrochloric acid in methanol are added. Stirring is carried out for 48 hours at ambient temperature, followed by evaporation to dryness. The residue is chromatographed on an Xterra LCMSprep column, eluting with acetonitrile/ammonium hydrogen carbonate buffer at 0.2% at a gradient. 4 mg of expected product, example 42, are thus recovered.

Example 43

Trans-N-[1-[2-[(4-aminocyclohexyl)amino]-9H-purin-6-yl]-2,3-dihydro-1H-indol-5-yl]-N'-(3,4-dichlorophenyl)urea

Stage 1: 1,1-dimethylethyl trans-6-[5-[[[(3,4-dichlorophenyl)amino]carbonyl]amino]-2,3-dihydro-1H-indol-1-yl]-2-[[4-[[(1,1-dimethylethoxy)carbonyl]amino]cyclohexyl]amino]-9H-purine-9-carboxylate 80 mg of product obtained in stage 4 of example 41 are mixed with 37.3 mg of 3,4-dichlorophenyl isocyanate and 5 ml of dichloromethane. Stirring is carried out for 2 hours at ambient temperature, 0.5 ml of water are added and the mixture is evaporated to dryness. Purification is carried out on an Xterra LCMSprep column, eluting with acetonitrile/ammonium hydrogen carbonate buffer, pH 9. 35 mg of expected product are obtained.

Stage 2: Trans-N-[1-[2-[(4-aminocyclohexyl)amino]-9H-purin-6-yl]-2,3-dihydro-1H-indol-5-yl]-N'-(3,4-dichlorophenyl)urea The product obtained in stage 1 is dissolved in 5 ml of methanol. 5 ml of a 2N solution of hydrochloric acid in methanol are added. Stirring is carried out for 48 hours at ambient temperature, followed by evaporation to dryness. The residue is chromatographed on an Xterra LCMSprep column, eluting with acetonitrile/ammonium hydrogen carbonate buffer at 0.2% as a gradient. 30 mg of expected product, example 43, are thus recovered.

Example 44

Trans-N-[6-(6-nitro-2,3-dihydro-1H-indol-1-yl)-9H-purin-2-yl]-1,4-cyclohexanediamine

Stage 1: 2-chloro-(6-nitro-2,3-dihydro-1H-indol-1-yl)-9H-purine 378 mg of 2,6-dichloropurine, 7 ml of butanol and 328 mg of 6-nitroindoline are mixed and brought to a temperature of 90° C. for approximately 3 days. The mixture is allowed to return to ambient temperature. Partial drying, washing with ethyl ether and drying under vacuum at 50° C. are carried out, and 573 mg of expected product are obtained, in the form of beige crystals.

Stage 2: Trans-N-[6-(6-nitro-2,3-dihydro-1H-indol-1-yl)-9H-purin-2-yl]-1,4-cyclohexanediamine 560 mg of product obtained in stage 1 above are mixed with 1.40 g of trans-1,4-diaminocyclohexane, and the mixture is then heated at 140° C. for approximately 55 hours. The mixture is allowed to return to ambient temperature. Purification is carried out by chromatography on silica with a CH2Cl2-MeOH—NH$_4$OH: 85-15-1.5 mixture for eluent. 197 mg of product are recovered, to which 10 ml of methanol/CH2Cl2 and 6 ml of HCl/ethanol are added. Partial drying and drying under vacuum at 35° C. are carried out. 27 mg of expected product are obtained.

Example 45

Trans-N-[1-[2-[(4-aminocyclohexyl)amino]-9H-purin-6-yl]-2,3-dihydro-1H-indol-5-yl]-N'-[4-(dimethylamino)phenyl]urea

Stage 1: 1,1-dimethylethyl trans-6-[5-[[[[4-(dimethyl-amino)phenyl]amino]carbonyl]amino]-2,3-dihydro-1H-indol-1-yl]-2-[[4-[[(1,1-dimethylethoxy)carbonyl]-amino]cyclohexyl]amino]-9H-purine-9-carboxylate 80 mg of product obtained in stage 4 of example 41 are mixed with 32.2 mg of 4-dimethylaminophenyl isocyanate and 5 ml of dichloromethane. Stirring is carried out for 20 hours at ambient temperature, 0.5 ml of water is added, and the mixture is evaporated to dryness. Purification is carried out on an Xterra LCMSprep column, eluting with acetonitrile/ammonium hydrogen carbonate buffer, pH 9. 55 mg of expected product are obtained.

Stage 2: Trans-N-[1-[2-[(4-aminocyclohexyl)amino]-9H-purin-6-yl]-2,3-dihydro-1H-indol-5-yl]-N'-[4-(dimethylamino)phenyl]urea The product obtained in stage 1 is dissolved in 5 ml of methanol. 5 ml of a 2N solution of hydrochloric acid in methanol are added. Stirring is carried out for 48 hours at ambient temperature, followed by evaporation to dryness. The residue is chromatographed on an Xterra LCMSprep column, eluting with aceto-nitrile/ammonium hydrogen carbonate buffer at 0.2% as a gradient. 42 mg of expected product, example 45, are thus obtained.

Example 46

Trans-N-[6-(5-amino-2,3-dihydro-1H-indol-1-yl)-9H-purin-2-yl]-1,4-cyclohexanediamine 200 mg of product obtained in stage 4 of example 41 are dissolved in 5 ml of methanol. 5 ml of a 2N solution of hydrochloric acid in methanol are added. Stirring is carried out for 48 hours at ambient temperature, followed by evaporation to dryness. The residue is chromatographed on a silica column, eluting with 85/15/1.5 dichloromethane/methanol/aqueous ammonia. The product obtained is taken up in 10 ml of a 50/50 methanol/dichloromethane mixture, 6 ml of 1M HCl solution in ethyl acetate are added, the mixture is left to crystallize, filtration is carried out, and 87 mg of expected product are thus recovered.

Example 47

Pharmaceutical Composition:

Tablets were prepared corresponding to the following formula:
Product of Example 1 . . . 0.2 g
Excipient for a finished tablet at . . . 1 g (details of the excipient: lactose, talc, starch, magnesium stearate).

Pharmacological Section:

The proteins used in the assays described below are obtained according to the usual methods known to those skilled in the art.

1) Assay for Inhibition of CIV-CDK (CIV1) Activity a) Preparation of the Reagents -(1)- 3× Enzyme Cocktail
967 µl buffer [50 mM Tris-HCl–0.1M NaCl–pH 7.5]–0.1% BSA+30 µl Cdk2 (1 mg/ml) +3 µl CaCiv1 (0.4 mg/ml)

-(2)- 3× Inhibitor Cocktail
A 3× range of inhibitor is prepared in 3% DMSO-buffer [50 mM Tris-HCl–0.1 M NaCl–pH 7.5]–0.1% BSA EXAMPLE of range: 200; 100; 30; 20; 10; 3; 2; 1; 0.3; 0 µM -(3)- 3×ATP Cocktail
12.2 µl [$^{33}$P]ATP+305 µl 10× kinase buffer+700 µl water
10× kinase buffer=0.5M Tris–0.1 M MgCl$_2$–1 mM Na$_3$VO$_4$–10 mM DTT–15 µM ATP–pH 7.5+1 tablet of protease inhibitors (Complete EDTA Free™ per 5 ml of buffer).

b) Carrying Out the Assay
1)—30 µl of the 3× enzyme cocktail (1) are mixed with 30 µl of the 3× inhibitor cocktail (2);
2)—30 µl of the 3×ATP cocktail (3) are added (start of the reaction);
3)—the mixture is incubated for 30 min at ambient temperature (20 to 25° C.);
4)—the reaction is stopped by adding 250 µl of buffer [50 mM Tris-HCl–0.1 M NaCl–pH 7.5]–0.1% BSA–25 mM EDTA;
5)—100 µl are distributed into a plate coated with antibodies directed against the substrate of the reaction;
6)—the plate is incubated for 60 min at ambient T°, with gentle agitation, and then washed 3 times with 300 µl of buffer [50 mM Tris-HCl–0.1 M NaCl–pH 7.5]–0.05% Tween 20;
9)—the plate is left to dry for 30 min at 37° C.;
10)—the plate is counted in a scintillation counter.

c) Results Obtained Expressed as IC50s Expressed as Micromolar

| Product | IC50 as micromolar |
| --- | --- |
| Example 1 | 0.8 |
| Example 2 | 0.5 |
| Example 5 | 1.1 |
| Example 7 | 3.6 |
| Example 8 | 1.3 |
| Example 15 | 0.3 |
| Example 16 | 0.31 |
| Example 18 | 3.9 |
| Example 19 | 0.78 |
| Example 20 | 1.7 |
| Example 24 | 0.39 |
| Example 27 | 4.3 |
| Example 30 | 0.1 |
| Example 39 | 3.6 |
| Example 40 | 0.2 |
| Example 41 | 0.95 |
| Example 42 | 3.3 |
| Example 43 | 4.4 |
| Example 44 | 0.02 |
| Example 45 | 1.3 |
| Example 46 | 2.00 |

2) Assay for Inhibition of SRC Kinase Activity

The inhibition is determined by fluorescence polarization, the Abl kinase phosphorylates a peptide detected by adding an anti-phosphopeptide antibody coupled to a fluorescent label.

The assay is carried out in a final volume of 50 µl; all the reagents are prepared in a buffer:
25 mM HEPES/NaOH pH 7.6
5 mM $MgCl_2$
2 mM $MnCl_2$
50 µM $Na_2VO_4$ 5 µl of the 10-times concentrated inhibitor are added to 25 µl of enzyme (12 U/ml final concentration), (Upstate Biotechnology ref 14-117). After incubation for 5 minutes at ambient temperature, 10 µl of PolyGluTyr 4/1 (150 ng/ml final concentration) and 10 µl of ATP (5 µM final concentration) are added. The detection is carried out after incubation for 20 minutes at ambient temperature.

Results obtained expressed as percentage inhibition at 20 µM
Example 8 98%
Example 15 99%
Example 20 99%
Example 24 99%
Example 27 95%
Example 30 99%
Example 32 100%
Example 38 95%

3) Assay for Inhibition of CDK2 Activity

The inhibition of the kinase activity of Cyclin Dependent kinase 2 (CDK2) is determined by measuring the phosphorylation of its substrate peptide.

The assay is carried out in a final volume of 50 µl.

The incubation buffer as follows:
50 mM Hepes/NaOH pH 7.5
10 mM $MgCl_2$
1 mM DTT 5 µl of the 10-times concentrated inhibitor are added to 25 µl of incubation buffer containing 0.8 U/µL final concentration of the enzyme; 10 µL of incubation buffer containing 0.0025 mg/ml of peptide substrate are then added and, finally, 10 µL of incubation buffer containing 2 mM ATP and radiolabeled ATP, [$^{33}$P]ATP (0.25 µCi), are added. The reaction is stopped after incubation for 10 minutes at 37° C.

Results obtained expressed as percentage inhibition at 20 µM
Example 2 97%
Example 27 97%
Example 30 99%

4) Assay for Inhibition of CDK1 Activity

The inhibition of the kinase activity of Cyclin Dependent kinase 1 (CDK1) is determined by measuring the phosphorylation of its substrate peptide.

The test is carried out in a final volume of 50 µl.

The incubation buffer is as follows:
50 mM Tris/HCl pH 7.5
10 mM $MgCl_2$
100 AM $Na_2VO_4$
2 mM DTT
40 mM Beta-glycerophosphate
0.1 mg/ml BSA 5 µl of the 10-times concentrated inhibitor are added to 25 µl of incubation buffer containing 0.04 U/µl final concentration of the enzyme; 10 µl of incubation buffer containing 12.5 µM final concentration of peptide substrate are then added and, finally, 10 µl of incubation buffer containing 50 µM ATP and radiolabeled ATP, [$^{33}$P]ATP (0.5 µCi), are added. The reaction is stopped after incubation for 40 minutes at ambient temperature.

Results obtained expressed as percentage inhibition at 20 µM
Example 8 93%
Example 30 99%

5) Assay for Inhibition of Abl Activity

The inhibition of the kinase activity is determined by fluorescence polarization, the Abl kinase phosphorylates a peptide detected by adding an anti-phosphopeptide antibody coupled to a fluorescent label.

The assay is carried out in a final volume of 50 µl; all the reagents are prepared in a buffer:
20 mM Hepes/NaOH pH 7.5
5 mM $MgCl_2$
100 µM $Na_2VO_4$
1 mM DTT
100 µM EDTA/NaOH
0.01% Brij35

5 µl of the 10-times concentrated inhibitor are added to 25 µl of enzyme (1000 U/ml final concentration), (Calbiochem ref 102555). After incubation for 5 minutes at ambient temperature, 10 µL of PolyGT (400 ng/ml final concentration) and 10 µL of ATP (5 µM final concentration) are added. The detection is carried out after incubation for 15 minutes at 30° C.

Results obtained expressed as percentage inhibition at 20 µM
Example 24 100%
Example 2 100%
Example 32 100%

6) Assay for Inhibition of ZAP Kinase Activity

The inhibition of the kinase activity is determined by fluorescence polarization, the ZAP kinase phosphorylates a peptide detected by adding an anti-phosphopeptide antibody coupled to a fluorescent label.

The assay is carried out in a final volume of 50 μl; all the reagents are prepared in a buffer:
20 mM Tris/HCl pH 7.7
7 mM MnCl$_2$
50 μM Na$_2$VO$_4$ 5 μl of the 10-times concentrated inhibitor are added to 25 μl of enzyme (0.7 μg/ml final concentration) (Panvera ref P2782). After incubation for 5 minutes at ambient temperature, 10 μl of PolyGT (300 ng/ml final concentration) and 10 μl of ATP (0.25 μM final concentration) are added. The detection is carried out after incubation for 15 minutes at ambient temperature.

Results obtained expressed as percentage inhibition at 20 μM
Example 8 98%
Example 20 95%
Example 24 96%

7) Assay for Inhibition of Casein Kinase II Activity

The inhibition of the kinase activity is determined by measuring the phosphorylation of its substrate peptide.

The assay is carried out in a final volume of 50 μl.

The incubation buffer is as follows:
30 mM MES pH 6.9
15 mM MgCl$_2$
195 mM KCl
7.25 mM DTT 5 μl of the 10-times concentrated inhibitor are added to 25 μl of incubation buffer containing 1 U/μl final concentration of the enzyme (Tebu, SE-124); 10 μl of incubation buffer containing 60 μM final concentration of peptide substrate are then added, and, finally, 10 μl of incubation buffer containing 25 μM ATP and radiolabeled ATP, [$^{33}$P]ATP (0.25 μCi), are added. The reaction is stopped after incubation for 30 minutes at ambient temperature.

Results obtained expressed as percentage inhibition at 20 μM
Example 8 93%
Example 30 97%

8) Assay for Inhibition for CAN Kinase II Activity

The inhibition of the kinase activity is determined by. measuring the phosphorylation of its substrate peptide.

The assay is carried out in a final volume of 50 μl.

The incubation buffer is as follows:
20 mM MOPS pH 7.4
5 mM MgCl$_2$
5 mM CaCl$_2$
1 mM DTT
100 μM Na$_2$VO$_4$
25 mM Beta-glycerophosphate 5 μl of the 10-times concentrated inhibitor are added to 25 μl of incubation buffer containing 0.2 μg/μl final concentration of the enzyme (Tebu, SE-134); 10 μl of incubation buffer containing 5 μM final concentration of substrate and 1600 U/ml final concentration of calmodulin are then added and, finally, 10 μl of incubation buffer containing 20 μM ATP and radiolabeled ATP, [$^{33}$P]ATP (0.05 μCi), are added. The reaction is stopped after incubation for 40 minutes at ambient temperature.

Results obtained expressed as percentage inhibition at 20 μM
Example 30 98%

9) Assay for Inhibition of EGF tyr Kinase Activity

The inhibition of the kinase activity is determined by measuring the phosphorylation of its substrate peptide.

The assay is carried out in a final volume of 100 μl.

The incubation buffer is as follows:
5 mM Hepes/Tris pH 7.4
2% Glycerol
0.2% triton X100

10 μl of the 10-times concentrated inhibitor are added to 20 μl of incubation buffer containing 1 U/μl final concentration of the enzyme (Tebu, SE-124); 30 μl of incubation buffer containing 0.43 mg/ml final concentration of peptide substrate are then added along with 20 μl of incubation buffer containing 0.4 μM of enzyme and, finally, 20 μl of 6 mM tris/HCl pH 7.4, 15 mM MgCl$_2$ buffer containing 10 μM ATP and radiolabeled ATP, [$^{33}$P]ATP (0.25 μCi), are added. The reaction is stopped after incubation for 60 minutes at 30° C.

Results obtained expressed as percentage inhibition at 20 μM
Example 20 100%

10) Assay for Inhibition of AKT Activity

The inhibition of the kinase activity is determined by fluorescence polarization, the AKT kinase phosphorylates a peptide detected by adding an anti-phosphopeptide antibody coupled to a fluorescent label.

The assay is carried out in a final volume of 30 μl; all the reagents are prepared in a buffer:
50 mM HEPES pH 7.5
0.03% triton X100
10 mM MgCl$_2$
5% Glycerol
1 mM DTT 10 μl of the 10-times concentrated inhibitor are added to 5 μl of enzyme (20 ng final concentration), and 5 μl of peptide (1 μM final concentration) and 10 μl of ATP (80 μM. final concentration) are added. The detection is carried out after incubation for 20 minutes at 25° C.

Results obtained expressed as IC50s expressed as micromolar
Example 8 0.46 μM

11) Assay for Inhibition of FAK Activity

The inhibition of the kinase activity is determined by fluorescence polarization, the autophosphorylation of FAK is detected by adding an anti-phosphoprotein antibody coupled to a fluorescent label.

The assay is carried out in a final volume of 30 μl; all the reagents are prepared in a buffer:
50 mM HEPES pH 7.5
0.03% triton X100
10 mM MgCl$_2$
5% Glycerol
1 mM DTT 10 μl of the 10-times concentrated inhibitor are added to 5 μl of enzyme (100 ng final concentration), and 5 μl of incubation buffer and 10 μl of ATP (1 μM final concentration) are added. The detection is carried out after incubation for 10 minutes at 25° C.

Results obtained expressed as IC50s expressed as micromolar
Example 8 2 μM
Example 20 1.6 μM
Example 30 1 μM 12) Assay for Inhibition of JNK3 Activity The inhibition of the kinase activity is determined by fluorescence polarization, the JNK3 kinase phosphorylates a peptide detected by adding an anti-phosphopeptide antibody coupled to a fluorescent label.

The assay is carried out in a final volume of 30 μl; all the reagents are prepared in a buffer:
50 mM HEPES pH 7.5
0.03% triton X100
10 mM $MgCl_2$
5% Glycerol
1 mM DTT 10 μl of the 10-times concentrated inhibitor are added to 5 μl of enzyme (40 ng final concentration), and 5 μl of incubation buffer containing 100 ng of substrate and 10 μl of ATP (6 μM final concentration) are added. The detection is carried out after incubation for 30 minutes at 25° C.

Results obtained expressed as IC50s expressed as micromolar
Example 8 0.84 μM
Example 1 0.29 μM
Example 15 0.5 μM
Example 38 0.42 μM
Example 26 0.31 μM
Example 27 0.29 μM 13) Assay for Inhibition of GSK3beta Activity The inhibition of the kinase activity is determined by measuring the phosphorylation of its substrate peptide.

The assay is carried out in a final volume of 40 μl; all the reagents are prepared in a buffer:
50 mM HEPES pH 7.5
0.03% triton X100
10 mM $MgCl_2$
5% Glycerol
1 mM DTT 10 μl of the 10-times concentrated inhibitor are added to 5 μl of enzyme (20 ng final concentration), and 5 μl of peptide (1 μM final concentration) then 2.5 μof incubation buffer containing 16 μM ATP and 2.5 μl of radiolabeled ATP, [$^{33}$P]ATP (50 nCi) are added. After incubation for 15 minutes at ambient temperature, 10 μl of incubation buffer containing 1 μM of substrate. The reaction is stopped after incubation for 30 minutes at 30° C.

Results obtained expressed as IC50s expressed as micromolar
Example 2 0.6 μM
Example 26 1.3 μM
Example 30 1.5 μM 14) Assay for Inhibition of PLK1 Activity The inhibition of the kinase activity is determined by measuring the phosphorylation of its substrate peptide.

The assay is carried out in a final volume of 40 μl; all the reagents are prepared in a buffer:
50 mM HEPES pH 7.5
0.03% triton X100
10 mM $MgCl_2$
5% Glycerol
1 mM DTT 10 μl of the 10-times concentrated inhibitor are added to 5 μl of enzyme (75 ng final concentration), and 5 μl of peptide (1 μM final concentration), then 2.5 μl of incubation buffer containing 40 μM ATP and 2.5 μl of radiolabeled ATP, [$^{33}$P]ATP (500 nCi), are added. After incubation for 15 minutes at ambient temperature, 10 μl of incubation buffer containing 192 nM of substrate. The reaction is stopped after incubation for 60 minutes at 37° C.

Results obtained expressed as IC50s expressed as micromolar
Example 18 0.16 μM
Example 1 0.21 μM 15) Determination of the Minimum Inhibitory Concentration in Order to Test the Sensitivity of Fungi to Antifungal Agents in Liquid Medium: Micro Method Principle: A constant number of cells of a given strain is placed in the presence of increasing concentrations of an antifungal agent, under conditions taken from the NCCLS (National Committee for Clinical Laboratory Standards, 1997. Reference method for broth dilution antifungal susceptibility testing of yeasts. Approved Standard M27-A. NCCLS, Villanova, Pa.); the minimum concentration with which a visible decrease is observed in the cloudiness of the cell growth (at least 80% compared to a control without product) is the Minimum Inhibitory Concentration (MIC) of the antifungal agent with respect to the strain tested.

RPMI 1640 medium (liquid) without L-glutamine is supplemented with L-glutamine (0.3 g/l or 10.5 ml of a solution at 200 mM) and buffered with 34.54 g/l (0.165 M) of morpholinepropanesulfonic acid (MOPS). The medium is sterilized by filtration. 100 μl of RPMI medium are distributed into each well of a 96-well plate. The appropriate volume. of the antifungal solution is distributed in the first column of the microplate and supplemented with 200 μl of medium. Doubling dilutions are made so as to establish a range of 11 concentrations in each line of the microplate. The 12th well of each row will serve as a growth control. The cell suspension is prepared from a culture (liquid or agar) or from a frozen vial, and is diluted in RPMI medium so as to obtain a cell suspension at $5\times10^3$–$2\times10^4$ cells/ml. 100 μl of the cell suspension are distributed in the microplate. For all species of *Candida*, the MIC is read after 24-48 h, and for *Cryptococcus* and *Aspergillus* after 48-72 h, of incubation at 37° C. in a normal atmosphere. The MIC is read by visual reading, determining the well which contains the lowest dose of antifungal agent which causes at least 80% inhibition of the growth of the fungus.

Results of the MICs

Example 5: MIC *Candida glabrata* 64 μg/ml; *Candida albicans* 64 μg/ml

Example 8: MIC *Candida glabrata* 16 μg/ml; *Candida albicans* 16 μg/ml; *Aspergillus fumigatus* 32 μg/ml Example 19: MIC *Candida glabrata* 32 μg/ml; *Candida albicans* 16 μg/ml; *Aspergillus fumigatus* 32 μg/ml Example 20: MIC *Candida glabrata* 16 μg/ml; *Candida albicans* 32 μg/ml; *Aspergillus fumigatus* 32 g/ml Example 30: MIC *Candida glabrata* 64 μg/ml; *Candida albicans* 32 μg/ml Example 32: MIC *Candida glabrata* 64 μg/ml; *Candida albicans* 64 μg/ml

The invention claimed is:
1. A product of formula (I):

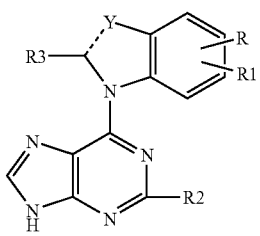

in which:
Y represents N, O, S, CHR3 or =CR3, the dashed line on the ring indicating that the corresponding bond is single or double;
R and R1, which may be identical or different, represent hydrogen, halogen, hydroxyl, alkyl, alkoxy, cyano, NO₂, NR4R5, trifluoromethyl, trifluoromethoxy, aryl, heteroaryl, —S(O)n-NR4R5, acyl, —NH—CO-alkyl or —NH—CO—NH-phenyl in which the alkyl and phenyl radicals are optionally substituted with one or more radicals chosen from thienyl and phenyl, itself optionally substituted, these phenyl radicals themselves being optionally substituted with one or more radicals chosen from halogen atoms and the radicals —NH2, —NHAlk and —N(Alk)2;
n represents an integer of 0 to 2,
R3 represents hydrogen, halogen, alkyl, cyano, NO₂, NR4R5, trifluoromethyl, or aryl,
R2 represents a radical alkyl, cycloalkyl, aryl, OR4, SR4 or NR4R5 in which R4 represents a hydrogen atom or an alkyl, cycloalkyl or aryl radical;
NR4R5 being such that either R4 and R5, which may be identical or different, are chosen from the values for R4, or R4 and R5 form, together with the nitrogen atom to which they are attached, a heterocyclic radical containing 4 to 6 ring members containing one or more hetero atoms, which may be identical or different, chosen from N, O and S;
all the alkyl, alkoxy, cycloalkyl, aryl and heterocyclic radicals defined above being optionally substituted with one or more radicals chosen from halogen atoms, hydroxyl, cyano, trifluoromethyl, trifluoromethoxy, alkoxy, aryl and heterocyclic radicals optionally substituted with a radical with an acid or acid isostere function; and the radicals —NHR4, —NalkR4, —COR4, —COOR4, CONalkR4 and —CONHR4, in which R4 represents a hydrogen atom or an alkyl, cycloalkyl or aryl radical, and alk represents an alkyl radical,
all the above phenylalkyl radicals being optionally substituted with one or more radicals chosen from halogen atoms, hydroxyl, cyano, trifluoromethyl, trifluoromethoxy, alkoxy, aryl and heterocyclic radicals optionally substituted with a radical with an acid or acid isostere function; and the radicals —NHR4, —NalkR4, —COR4, —COOR4, —CONalkR4 and —CONHR4, in which R4 represents a hydrogen atom or an alkyl, cycloalkyl or aryl radical, and alk represents an alkyl radical;
all the aryl and heterocyclic radicals defined above also being optionally substituted with one or more alkyl, hydroxyalkyl and phenylalkyl radicals;
all the aryl radicals defined above also being optionally substituted with a dioxolyl radical;
all the alkyl and alkoxy radicals defined above being linear or branched and containing at most 6 carbon atoms;
all the cycloalkyl radicals defined above containing at most 6 carbon atoms;
wherein the acid or acid isostere function represents a free, salified or esterified carboxyl radical, a free or salified tetrazolyl radical, or a radical selected from the group consisting of —SO3H, —PO(OH)2, NH—SO2-CF3, —NH—SO2-NH—V, NH—SO2-NH—CO—V, NH—CO—V, —NH—CO—NH—V, —NH—CO—NH—SO2-V, —SO2-NH—CO—V, —SO2-NH—CO—NH—V, —CO—NH—V, —CO—NH—OH, —CO—NH—SO2-V; V represents a linear or branched alkyl or alkenyl radical containing at most 6 carbon atoms or a phenyl radical; said alkyl, alkenyl and phenyl radicals represented by V optionally being substituted with one or more radicals chosen from halogen atoms, hydroxyl, cyano, trifluoromethyl, trifluoromethoxy, alkoxy, aryl, heterocyclic, —NHR4, —NalkR4, —COR4, —COOR4, —CONalkR4 and —CONHR4 radicals, in which R4 represents a hydrogen atom or an alkyl, cycloalkyl or aryl radical and alk represents an alkyl;
said compounds of formula (I) being in all the possible racemic, enantiomeric and diastereoisomeric isomer forms; or a pharmaceutically acceptable addition salt with an inorganic or organic acid or with an inorganic or organic base of said compound of formula (I).

2. A compound of formula (I) according to claim 1:

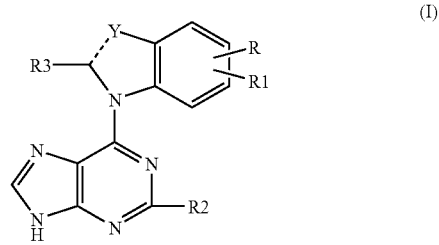

in which:
Y represents N, O, S, CHR3 or =CR3, the dashed line on the ring indicating that the corresponding bond is single or double;
R and R1, which may be identical or different, represent hydrogen, halogen, hydroxyl, alkyl, alkoxy, cyano, NO₂, NR4R5, trifluoromethyl, trifluoromethoxy, aryl, heteroaryl, or —S(O)n-NR4R5;
n represents an integer of 0 to 2;
R3 represents hydrogen, halogen, alkyl, cyano, NO₂, NR4R5, trifluoromethyl, or aryl;
R2 represents a radical alkyl, cycloalkyl, aryl, OR4, SR4 or NR4R5 in which R4 represents a hydrogen atom or an alkyl, cycloalkyl or aryl radical;
NR4R5 being such that either R4 and R5, which may be identical or different, are chosen from the values for R4, or R4 and R5 form, together with the nitrogen atom to which they are attached, a heterocyclic radical containing 4 to 6 ring members containing one or more hetero atoms, which may be identical or different, chosen from N, O and S;
all the alkyl, alkoxy, cycloalkyl, aryl and heterocyclic radicals defined above being optionally substituted with one or more radicals chosen from halogen atoms, hydroxyl, cyano, trifluoromethyl, trifluoromethoxy, alkoxy, aryl and heterocyclic radicals optionally substituted with a radical with an acid or acid isostere function and the radicals —NHR4, —NalkR4, —COR4, —COOR4, —CONalkR4 and —CONHR4 in which R4 represents a hydrogen atom or an alkyl, cycloalkyl or aryl radical, and alk represents an alkyl radical;

all the aryl and heterocyclic radicals defined above also being optionally substituted with one or more alkyl, hydroxyalkyl and phenylalkyl radicals;

all the aryl radicals defined above also being optionally substituted with a dioxolyl radical;

all the alkyl and alkoxy radicals defined above being linear or branched and containing at most 6 carbon atoms;

all the cycloalkyl radicals defined above containing at most 6 carbon atoms;

wherein the acid or acid isostere function represents a free, salified or esterified carboxyl radical, a free or salified tetrazolyl radical, or a radical selected from the group consisting of —SO3H, —PO(OH)2, NH—SO2-CF3, —NH—SO2-NH—V, NH—SO2-NH—CO—V, NH—CO—V, —NH—CO—NH—V, —NH—CO—NH—SO2-V, —SO2-NH—CO—V, —SO2-NH—CO—NH—V, —CO—NH—V, —CO—NH—OH, —CO—NH—SO2-V; V represents a linear or branched alkyl or alkenyl radical containing at most 6 carbon atoms or a phenyl radical; said alkyl, alkenyl and phenyl radicals represented by V optionally being substituted with one or more radicals chosen from halogen atoms, hydroxyl, cyano, trifluoromethyl, trifluoromethoxy, alkoxy, aryl, heterocyclic, —NHR4, —NalkR4, —COR4, —COOR4, —CONalkR4 and —CONHR4 radicals, in which R4 represents a hydrogen atom or an alkyl, cycloalkyl or aryl radical, and alk represents an alkyl;

said compounds of formula (I) being in all the possible racemic, enantiomeric and diastereoisomeric isomer forms, or a pharmaceutically acceptable addition salt with an inorganic or organic acid or with an inorganic or organic base of said compound of formula (I).

3. A compound of formula (I) according to claim 1, corresponding to formula (Ia):

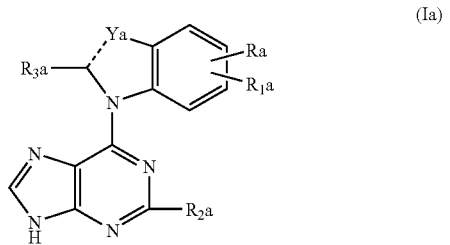

(Ia)

in which:

Ya represents N, O, S, CHR3a or =CR3a, the dashed line on the ring indicating that the corresponding bond is single or double;

Ra and R1a, which may be identical or different, represent hydrogen, halogen, hydroxyl, alkyl, alkoxy, cyano, NO$_2$, NR4aR5a, trifluoromethyl, trifluoromethoxy, phenyl, heteroaryl, or —S(O)n-NR4aR5a;

n represents an integer of 0 to 2;

R3a represents hydrogen, halogen, alkyl, cyano, NO$_2$, amino, alkylamino, dialkylamino, trifluoromethyl or phenyl;

R2a represents a radical alkyl, cycloalkyl, phenyl, OR4a, SR4a or NR4aR5a, in which R4a represents a hydrogen atom or an alkyl, cycloalkyl or phenyl radical;

NR4aR5a being such that either R4a and R5a, which may be identical or different, are chosen from the values for R4a, or R4a and R5a form, together with the nitrogen atom to which they are attached, an optionally substituted heterocyclic radical selected from piperidyl, morpholinyl, pyrrolidinyl or piperazinyl radical;

all the alkyl, alkoxy, cycloalkyl, phenyl, phenylalkyl and heterocyclic radicals defined above being optionally substituted with one or more radicals chosen from halogen atoms, hydroxyl, cyano, trifluoromethyl, trifluoromethoxy, alkoxy and phenyl radicals, a heterocyclic radical optionally substituted on N or C with a carboxyl radical which is free, salified or esterified with an alkyl radical, the radicals SO$_3$H, PO(OH)$_2$, NH—SO$_2$—CF$_3$, NH—SO$_2$—NH—V and NH—SO$_2$—NH—CO—V in which V represents a phenyl, alkyl or alkenyl radical, the alkenyl radicals being linear or branched containing at most 6 carbon atoms; and the radicals —NalkR4a, —NHR4a, —COR4a, —COOR4a, —CONalkR4a and —CONHR4a in which R4a represents a hydrogen atom or an alkyl, cycloalkyl or phenyl radical, and alk represents an alkyl radical;

all the phenyl and heterocyclic radicals defined above also being optionally substituted with one or more alkyl, hydroxyalkyl or phenylalkyl radicals;

all the phenyl radicals defined above also being optionally substituted with a dioxolyl radical;

all the alkyl and alkoxy radicals defined above being linear or branched and containing at most 6 carbon atoms;

all the cycloalkyl radicals defined above containing 5 or 6 carbon atoms;

said compounds of formula (Ia) being in all the possible racemic, enantiomeric and diastereoisomeric isomer forms; or a pharmaceutically acceptable addition salt with an inorganic or organic acid or with an inorganic or organic base of said compound of formula (Ia).

4. A compound of formula (I) according to claim 1, corresponding to formula (Ib):

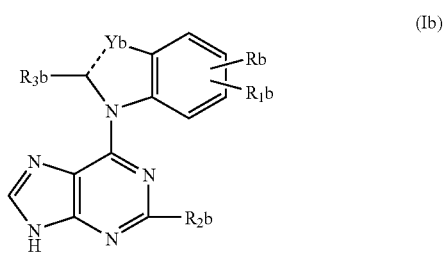

(Ib)

in which:

Yb represents N, CHR3b or =CR3b, the dashed line on the ring indicating that the corresponding bond is single or double;

Rb and R1b, which may be identical or different, represent hydrogen, halogen, hydroxyl, alkyl, alkoxy, cyano, NO$_2$, trifluoromethyl, trifluoromethoxy, phenyl, or —S(O)n-NR4bR5b;

n represents an integer of 0 to 2;

R3b represents hydrogen, halogen, alkyl, cyano, NO$_2$, amino, alkylamino, dialkylamino, trifluoromethyl or phenyl;

R2b represents a radical alkyl, cycloalkyl, phenyl, or NR4bR5b, in which R4b represents a hydrogen atom or an alkyl, cycloalkyl or phenyl radical;

NR4bR5b being such that either R4b and R5b, which may be identical or different, are chosen from the values for R4b, or R4b and R5b form, together with the nitrogen atom to which they are attached, an optionally substituted heterocyclic radical selected from piperidyl, morpholinyl or pyrrolidinyl radical;

all the alkyl, alkoxy, cycloalkyl, phenyl and phenylalkyl radicals and heterocyclic radicals, defined above being optionally substituted with one or two radicals chosen from halogen atoms, hydroxyl, cyano, trifluoromethyl, trifluoromethoxy, alkoxy and phenyl radicals, and tetrahydropyranyl and piperidyl radicals, themselves optionally substituted on N or C with a carboxyl radical which is free, salified or esterified with an alkyl radical; and the radicals —NalkR4a, —NHR4a and —COOR4a in which R4a represents a hydrogen atom or an alkyl, cycloalkyl or phenyl radical, and alk represents an alkyl radical;

all the phenyl and heterocyclic radicals defined above also being optionally substituted with one or more alkyl, hydroxyalkyl and phenylalkyl radicals;

all the alkyl and alkoxy radicals defined above being linear or branched and containing at most 4 carbon atoms;

all the cycloalkyl radicals defined above containing 5 or 6 carbon atoms;

said compounds of formula (Ib) being in all the possible racemic, enantiomeric and diastereoisomeric isomer forms, or a pharmaceutically acceptable addition salt with an inorganic or organic acid or with an inorganic or organic base of said compound of formula (Ib).

5. A compound of formula (I) according to claim 1, corresponding to formula (Ic):

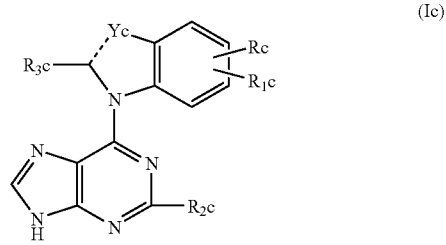

(Ic)

in which:

Yc represents N, CH$_2$ or CH═, the dashed line on the ring indicating that the corresponding bond is single or double;

Rc and R1c, which may be identical or different, represent hydrogen, halogen, hydroxyl, alkyl, alkoxy, phenylalkoxy, phenylalkyl, cyano, NO$_2$, trifluoromethyl, trifluoromethoxy, phenyl, —S(O)n-NH$_2$, —S(O)n-NHAlk, or —S(O)n-N(Alk)2; and n represents an integer of 0 to 2;

R3c represents hydrogen, halogen, alkyl, cyano, NO$_2$, trifluoromethyl or phenyl;

R2c represents a radical NR4cR5c in which either R4c and R5c, which may be identical or different, are such that R4c represents a hydrogen atom or an alkyl, cycloalkyl, phenyl or phenylalkyl radical;

the alkyl, cycloalkyl, phenyl and phenylalkyl radicals being optionally substituted with one or more radicals chosen from hydroxyl, amino or carboxyl which is free, salified or esterified with an alkyl radical, tetrahydropyranyl radical or piperidyl radical, optionally substituted on N or C with a carboxyl radical which is free, salified or esterified with an alkyl radical;

and R5c represents a hydrogen atom or an alkyl radical, or R4c and R5c form, together with the nitrogen atom to which they are attached, a piperidyl, morpholinyl or pyrrolidinyl radical, these radicals being optionally substituted with an alkyl, hydroxyalkyl, amino, monoalkylamino or dialkylamino radical;

Alk represents an alkyl radical;

all the alkyl and alkoxy radicals defined above being linear or branched containing at most 4 carbon atoms;

said compounds of formula (Ic) being in all the possible racemic, enantiomeric and diastereoisomeric isomer forms, or a pharmaceutically acceptable addition salt with an inorganic or organic acid or with an inorganic or organic base of said compound of formula (Ic).

6. A compound of formula (I) according to claim 1, corresponding to formula (Id):

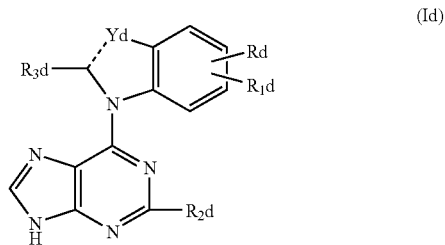

(Id)

in which:

Yd represents N, CH$_2$ or CH═, the dashed line on the ring indicating that the corresponding bond is single or double;

Rd and R1d, which may be identical or different, represent hydrogen, halogen, alkyl, alkoxy, phenylalkoxy, NO$_2$, dialkylaminosulfonyl, —NH$_2$, trifluoromethyl, —CO—CH3, —NH—CO-alkyl or —NH—CO—NH-phenyl in which the alkyl radical is optionally substituted with a thienyl or phenyl radical and the phenyl radical is optionally substituted with one or more radicals chosen from halogen atoms and the radicals —NH2, —NHAlk and —N(Alk)2;

R3d represents hydrogen or alkyl;

R2d represents a radical NR4dR5d in which either R4d and R5d, which may be identical or different, are such that R4d represents a hydrogen atom, a linear or branched alkyl radical containing 1 to 4 carbon atoms and optionally substituted with one or two hydroxyl(s), a cycloalkyl radical optionally substituted with an amino or hydroxyl radical, or R4d represents a phenyl or phenylalkyl (1 to 4 C) radical with phenyl optionally substituted with a carboxyl radical which is free, salified or esterified with an alkyl radical, or R4d represents a tetrahydropyranalkyl radical or a piperidylalkyl radical optionally substituted on N or C with a carboxyl radical, and R5d represents a hydrogen atom or an alkyl radical, or R4d and R5d form, together with the nitrogen atom to which they are attached, a piperidyl radical optionally substituted with an amino radical, a morpholinyl radical or a pyrrolidinyl radical optionally substituted with a hydroxyalkyl radical;

all the alkyl and alkoxy radicals defined above being linear or branched containing at most 4 carbon atoms:

said compounds of formula (Id) being in all the possible racemic, enantiomeric and diastereoisomeric isomer forms, or a pharmaceutically acceptable addition salt with an inorganic or organic acid or with an inorganic or organic base of said compound of formula (Id).

7. A compound of formula (I) according to claim 1, corresponding to formula (Id):

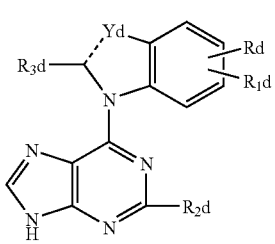

(Id)

in which:

Yd represents N, CH₂ or CH=, the dashed line on the ring indicating that the corresponding bond is single or double;

Rd and R1d, which may be identical or different, represent hydrogen, halogen, alkyl, alkoxy, phenylalkoxy, NO₂, or dialkylaminosulfonyl;

R3d represents hydrogen or alkyl;

R2d represents a radical NR4dR5d in which either R4d and R5d, which may be identical or different, are such that R4d represents a hydrogen atom, a linear or branched alkyl radical containing 1 to 4 carbon atoms and optionally substituted with one or two hydroxyl(s), a cycloalkyl radical optionally substituted with an amino or hydroxyl radical, or R4d represents a phenyl or phenylalkyl (1 to 4 C) radical with phenyl optionally substituted with a carboxyl radical which is free, salified or esterified with an alkyl radical, or R4d represents a tetrahydropyranalkyl radical or a piperidylalkyl radical optionally substituted on N or C with a carboxyl radical, and R5d represents a hydrogen atom or an alkyl radical, or R4d and R5d form, together with the nitrogen atom to which they are attached, a piperidyl radical optionally substituted with an amino radical, a morpholinyl radical or a pyrrolidinyl radical optionally substituted with a hydroxyalkyl radical;

all the alkyl and alkoxy radicals defined above being linear or branched containing at most 4 carbon atoms:

said compounds of formula (Id) being in all the possible racemic, enantiomeric and diastereoisomeric isomer forms, or a pharmaceutically acceptable addition salt with an inorganic or organic acid or with an inorganic or organic base of said compound of formula (Id).

8. A compound of formula (I) according to claim 1, selected from the group consisting of:
trans-N-[6-(5,6-dichloro-2,3-dihydro-1H-indol-1-yl)-9H-purin-2-yl]-1,4-cyclohexanediamine dihydrochloride;
trans-N-[6-(1H-benzimidazol-1-yl)-9H-purin-2-yl]-1,4-cyclohexanediamine dihydrochloride;
trans-N-[6-(5,6-dimethyl-1H-benzimidazol-1-yl)-9H-purin-2-yl]-1,4-cyclohexanediamine;
trans-N-[6-(5,6-dichloro-1H-benzimidazol-1-yl)-9H-purin-2-yl]-1,4-cyclohexanediamine hydrochloride;
trans-N-[6-(5-methoxy-1H-benzimidazol-1-yl)-9H-purin-2-yl]-1,4-cyclohexanediamine dihydrochloride;
trans-N-[6-(1H-indol-1-yl)-9H-purin-2-yl]-1,4-cyclohexanediamine dihydrochloride;
trans-N-[6-[6-(phenylmethoxy)-1H-benzimidazol-1-yl]-9H-purin-2-yl]-1,4-cyclohexanediamine;
trans-N-[6-[5-(phenylmethoxy)-1H-benzimidazol-1-yl]-9H-purin-2-yl]-1,4-cyclohexanediamine;
trans-4-[[6-(1H-benzimidazol-1-yl)-9H-purin-2-yl]amino]cyclohexanol;
trans-N-[6-(2,3-dihydro-5-nitro-1H-indol-1-yl)-9H-purin-2-yl]-1,4-cyclohexanediamine dihydrochloride;
trans-N-6-(2,3-dihydro-6-(trifluoromethyl)-1H-indol-1-yl)-9H-purin-2-yl]-1,4-cyclohexanediamine;
trans-N-[1-[2-[(4-aminocyclohexyl)amino]-9H-purin-6-yl]-2,3-dihydro-1H-indol-5-yl]-2-thiopheneacetamide; and
trans-N-[6-(6-nitro-2,3-dihydro-1H-indol-1-yl)-9H-purin-2-yl]-1,4-cyclohexanediamine.

9. A pharmaceutical composition containing, as active principle, at least one compound according to any one of claims 1 to 6, and a pharmaceutically acceptable excipient.

10. A compound of formula (IV)

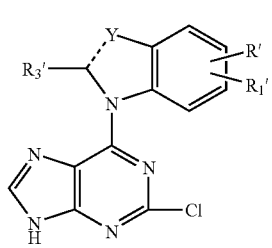

(IV)

in which:

Y represents N, O, S, CHR3 or =CR3, the dashed line on the ring indicating that the corresponding bond is single or double;

R' and R1', which may be identical or different, represent hydrogen, halogen, hydroxyl, alkyl, alkoxy, cyano, NO₂, NR4R5, trifluoromethyl, trifluoromethoxy, aryl, heteroaryl, —S(O)n-NR4R5, acyl, —NH—CO-alkyl or NH—CO—NH-phenyl in which the alkyl and phenyl radicals are optionally substituted with one or more radicals chosen from thienyl and phenyl, itself optionally substituted, these phenyl radicals themselves being optionally substituted with one or more radicals chosen from halogen atoms and the radicals NH2, —NHAlk and —N(Alk); n represents an integer of 0 to 2;

R3' represents hydrogen, halogen, alkyl, cyano, NO₂, NR4R5, trifluoromethyl, or aryl, NR4R5 being such that either R4 and R5, which may be identical or different, are chosen from hydrogen atom or an alkyl, cycloalkyl or aryl radical; or R4 and R5 form, together with the nitrogen atom to which they are attached, a heterocyclic radical containing 4 to 6 ring members containing one or more hetero atoms, which may be identical or different, chosen from N, O and S;

all the alkyl, alkoxy, cycloalkyl, aryl and heterocyclic radicals defined above being optionally substituted with one or more radicals chosen from halogen atoms, hydroxyl, cyano, trifluoromethyl, trifluoromethoxy, alkoxy, aryl and heterocyclic radicals optionally substituted with a radical with an acid or acid isostere function and the radicals —NHR4, —NalkR4, —COR4, —COOR4, —CONalkR4 and —CONHR4, in which R4 represents a hydrogen atom or an alkyl, cycloalkyl or aryl radical, and alk represents an alkyl radical;

all the above phenylalkyl radicals being optionally substituted with one or more radicals chosen from halogen atoms, hydroxyl, cyano, trifluoromethyl, trifluoromethoxy, alkoxy, aryl and heterocyclic radicals optionally substituted with a radical with an acid or acid isostere function; and the radicals —NHR4, —NalkR4, —COR4, —COOR4, —CONalkR4 and —CONHR4, in which R4 represents a hydrogen atom or an alkyl, cycloalkyl or aryl radical, and alk represents an alkyl radical;

all the aryl and heterocyclic radicals defined above also being optionally substituted with one or more alkyl, hydroxyalkyl and phenylalkyl radicals;

all the aryl radicals defined above also being optionally substituted with a dioxolyl radical;

all the alkyl and alkoxy radicals defined above being linear or branched and containing at most 6 carbon atoms;

all the cycloalkyl radicals defined above containing at most 6 carbon atoms;

wherein the acid or acid isostere function represents a free, salified or esterified carboxyl radical, a free or salified tetrazolyl radical, or a radical selected from the group consisting of —SO3H, —PO(OH)2, NH—SO2-CF3, —NH—SO2-NH—V, NH—SO2-NH—CO—V, NH—CO—V, —NH—CO—NH—V, —NH—CO—NH—SO2-V, —SO2-NH—CO—V, —SO2-NH—CO—NH—V, —CO—NH—V, —CO—NH—OH, —CO—NH—SO2-V; V represents a linear or branched alkyl or alkenyl radical containing at most 6 carbon atoms or a phenyl radical; said alkyl, alkenyl and phenyl radicals represented by V optionally being substituted with one or more radicals chosen from halogen atoms, hydroxyl, cyano, trifluoromethyl, trifluoromethoxy, alkoxy, aryl, heterocyclic, —NHR4, —NalkR4, —COR4, —COOR4, —CONalkR4 and —CONHR4 radicals, in which R4 represents a hydrogen atom or an alkyl, cycloalkyl or aryl radical, and alk represents an alkyl radical.

11. A compound of formula (I):

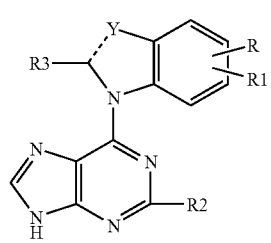

(I)

in which:

Y represents N, O, S, or CHR3, the dashed line on the ring indicating that the corresponding bond is single or double;

R and R1, which may be identical or different, represent hydrogen, halogen, hydroxyl, alkyl, alkoxy, cyano, NO$_2$, NR4R5, trifluoromethyl, trifluoromethoxy, aryl, heteroaryl, —S(O)n-NR4R5, acyl, —NH—CO-alkyl or —NH—CO—NH-phenyl in which the alkyl and phenyl radicals are optionally substituted with one or more radicals chosen from thienyl and phenyl, itself optionally substituted, these phenyl radicals themselves being optionally substituted with one or more radicals chosen from halogen atoms and the radicals —NH2, —NHAlk and —N(Alk)2;

n represents an integer of 0 to 2;

R3 represents hydrogen, halogen, alkyl, cyano, NO$_2$, NR4R5, trifluoromethyl, or aryl;

R2 represents a radical R4, OR4, SR4 or NR4R5, in which R4 represents a hydrogen atom or an alkyl, cycloalkyl or aryl radical;

NR4R5 being such that either R4 and R5, which may be identical or different, are chosen from the values for R4, or R4 and R5 form, together with the nitrogen atom to which they are attached, a heterocyclic radical containing 4 to 6 ring members containing one or more hetero atoms, which may be identical or different, chosen from N, O and S;

all the alkyl, alkoxy, cycloalkyl, aryl and heterocyclic radicals defined above being optionally substituted with one or more radicals chosen from halogen atoms, hydroxyl, cyano, trifluoromethyl, trifluoromethoxy, alkoxy, aryl and heterocyclic radicals optionally substituted with a radical with an acid or acid isostere function; and the radicals —NHR4, —NalkR4, —COR4, —COOR4, —CONalkR4 and —CONHR4, in which R4 represents a hydrogen atom or an alkyl, cycloalkyl or aryl radical, and alk represents an alkyl radical;

all the above phenylalkyl radicals being optionally substituted with one or more radicals chosen from halogen atoms, hydroxyl, cyano, trifluoromethyl, trifluoromethoxy, alkoxy, aryl and heterocyclic radicals optionally substituted with a radical with an acid or acid isostere function;

and the radicals —NHR4, —NalkR4, —COR4, —COOR4, —CONalkR4 and —CONHR4, in which R4 represents a hydrogen atom or an alkyl, cycloalkyl or aryl radical, and alk represents an alkyl radical;

all the aryl and heterocyclic radicals defined above also being optionally substituted with one or more alkyl, hydroxyalkyl and phenylalkyl radicals;

all the aryl radicals defined above also being optionally substituted with a dioxolyl radical;

all the alkyl and alkoxy radicals defined above being linear or branched and containing at most 6 carbon atoms;

all the cycloalkyl radicals defined above containing at most 6 carbon atoms;

wherein the acid or acid isostere function represents a free, salified or esterified carboxyl radical, a free or salified tetrazolyl radical, or a radical selected from the group consisting of —SO3H, —PO(OH)2, NH—SO2-CF3, —NH—SO2-NH—V, NH—SO2-NH—CO—V, NH—CO—V, —NH—CO—NH—V, —NH—CO—

NH—SO2-V, —SO2-NH—CO—V, —SO2-NH—CO—NH—V, —CO—NH—V, —CO—NH—OH, —CO—NH—SO2-V; V represents a linear or branched alkyl or alkenyl radical containing at most 6 carbon atoms or a phenyl radical; said alkyl, alkenyl and phenyl radicals represented by V optionally being substituted with one or more radicals chosen from halogen atoms, hydroxyl, cyano, trifluoromethyl, trifluoromethoxy, alkoxy, aryl, heterocyclic, —NHR4, —NalkR4, —COR4, —COOR4, —CONalkR4 and —CONHR4 radicals, in which R4 represents a hydrogen atom or an alkyl, cycloalkyl or aryl radical and alk represents an alkyl;

said compounds of formula (I) being in all the possible racemic, enantiomeric and diastereoisomeric isomer forms; or a pharmaceutically acceptable addition salt with an inorganic or organic acid or with an inorganic or organic base of said compound of formula (I).

* * * * *